(12) United States Patent
Cuevas et al.

(10) Patent No.: US 11,920,170 B2
(45) Date of Patent: Mar. 5, 2024

(54) ALPHA-AMYLASE COMBINATORIAL VARIANTS

(71) Applicant: Danisco US Inc., Palo Alto, CA (US)

(72) Inventors: William Cuevas, Palo Alto, CA (US); Vivek Sharma, Palo Alto, CA (US); David E. Wildes, Palo Alto, CA (US); Sang-Kyu Lee, Palo Alto, CA (US); Dina Finan, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 16/060,506

(22) PCT Filed: Dec. 9, 2016

(86) PCT No.: PCT/US2016/066031
§ 371 (c)(1),
(2) Date: Jun. 8, 2018

(87) PCT Pub. No.: WO2017/100720
PCT Pub. Date: Jun. 15, 2017

(65) Prior Publication Data
US 2019/0144842 A1 May 16, 2019

Related U.S. Application Data

(60) Provisional application No. 62/265,301, filed on Dec. 9, 2015.

(51) Int. Cl.
| | |
|---|---|
| C12P 19/14 | (2006.01) |
| C11D 3/386 | (2006.01) |
| C12N 9/26 | (2006.01) |
| C12N 9/28 | (2006.01) |

(52) U.S. Cl.
CPC ............ *C12N 9/2417* (2013.01); *C11D 3/386* (2013.01); *C12N 9/2414* (2013.01); *C12P 19/14* (2013.01); *C12Y 302/01001* (2013.01)

(58) Field of Classification Search
CPC ............ C12Y 302/01001; C12P 19/14; C12N 9/2414
USPC .......................................................... 435/188
See application file for complete search history.

(56) References Cited

U.S. PATENT DOCUMENTS

| | | | |
|---|---|---|---|
| 4,106,991 | A | 8/1978 | Markussen et al. |
| 4,435,307 | A | 3/1984 | Barbesgaard et al. |
| RE32,153 | E | 5/1986 | Tamura et al. |
| 4,587,215 | A | 5/1986 | Hirsch |
| 4,661,452 | A | 4/1987 | Markussen et al. |
| 5,281,526 | A | 1/1994 | Good et al. |
| RE34,606 | E | 5/1994 | Estell et al. |
| 5,340,735 | A | 8/1994 | Christianson et al. |
| 5,422,267 | A | 6/1995 | Yocum et al. |
| 5,457,046 | A | 10/1995 | Woldike et al. |
| 5,500,364 | A | 3/1996 | Christianson et al. |
| 5,648,263 | A | 7/1997 | Schulein et al. |
| 5,686,593 | A | 11/1997 | Woldike et al. |
| 5,691,178 | A | 11/1997 | Schulein et al. |
| 5,700,676 | A | 12/1997 | Bott et al. |
| 5,763,254 | A | 6/1998 | Woldike et al. |
| 5,776,757 | A | 7/1998 | Schulein et al. |
| 5,801,039 | A | 9/1998 | Maurer et al. |
| 5,855,625 | A | 1/1999 | Maurer et al. |
| 5,955,340 | A | 9/1999 | Bott et al. |
| 6,077,316 | A | 6/2000 | Lund et al. |
| 6,312,936 | B1 | 11/2001 | Poulose et al. |
| 6,376,450 | B1 | 4/2002 | Ghosh et al. |
| 6,482,628 | B1 | 11/2002 | Poulose et al. |
| 6,730,646 | B1 | 5/2004 | Waschenbach et al. |
| 6,933,140 | B1 | 8/2005 | Dyson et al. |
| 7,001,878 | B2 | 2/2006 | Buzzaccarni et al. |
| 2006/0094080 | A1 | 5/2006 | Dunn-Coleman et al. |
| 2007/0004018 | A1 | 1/2007 | Dunn-Coleman et al. |
| 2007/0015266 | A1 | 1/2007 | Dunn-Coleman et al. |
| 2008/0090747 | A1 | 4/2008 | Augustinus et al. |
| 2009/0209445 | A1 | 8/2009 | Panandiker et al. |
| 2010/0081598 | A1 | 4/2010 | Sharma et al. |
| 2015/0141316 | A1 | 5/2015 | Bott et al. |
| 2015/0152401 | A1 | 6/2015 | Cascao-Pereira et al. |
| 2016/0017303 | A1 | 1/2016 | Cascao-Pereira et al. |
| 2016/0017304 | A1 | 1/2016 | Cascao-Pereira et al. |
| 2016/0017305 | A1 | 1/2016 | Cascao-Pereira et al. |
| 2016/0272957 | A1 | 9/2016 | Finan |
| 2017/0037387 | A1* | 2/2017 | Cascao-Pereira ............ C11D 11/0023 |

FOREIGN PATENT DOCUMENTS

| | | |
|---|---|---|
| EP | 0135138 A2 | 3/1985 |
| EP | 0238216 B1 | 5/1990 |
| EP | 0407225 A1 | 1/1991 |
| EP | 0218272 B1 | 3/1992 |

(Continued)

OTHER PUBLICATIONS

Fogarty et al., Starch-Degrading Enzymes of Microbial Origin, In Progress in Industrial Microbiology, 1979, vol. 15, pp. 112-115.

Jeang et al., Cloning of a Gene Encoding Raw-Starch-Digesting Amylase from a *Cytophaga* sp. and its Expression in *Escherichia coli*, Applied and Environmental Microbiology, 2002, vol. 68, pp. 3651-3654.

Shiau et al., Improving the Thermostability of Raw-Starch-Digesting Amylase from a *Cytophaga* sp., by Site-Directed Mutagenesis, Applied and Environmental Microbiology, 2003, vol. 69, pp. 2383-2385.

(Continued)

*Primary Examiner* — Tekchand Saidha

(57) ABSTRACT

Disclosed are compositions and methods relating to variant alpha-amylases. The variant alpha-amylases are useful, for example, for starch liquefaction and saccharification, for cleaning starchy stains in laundry, dishwashing, and other applications, for textile processing (e.g., desizing), in animal feed for improving digestibility, and for baking and brewing.

11 Claims, 2 Drawing Sheets

Specification includes a Sequence Listing.

(56) References Cited

FOREIGN PATENT DOCUMENTS

| | | | |
|---|---|---|---|
| EP | 0260105 B1 | 5/1994 |
| EP | 0258068 B1 | 8/1994 |
| EP | 0531372 B1 | 2/1995 |
| EP | 0305216 B1 | 8/1995 |
| EP | 0531315 B1 | 3/1997 |
| EP | 0331376 B1 | 10/1997 |
| EP | 0495257 B1 | 6/2002 |
| EP | 1504994 B1 | 7/2007 |
| EP | 1740690 B1 | 10/2012 |
| GB | 1372034 A | 10/1974 |
| GB | 1483591 A | 8/1977 |
| JP | 64744992 | 3/1989 |
| WO | 8402921 A2 | 8/1984 |
| WO | 8601831 A1 | 3/1986 |
| WO | 8906270 A1 | 7/1989 |
| WO | 8906279 A1 | 7/1989 |
| WO | 8909259 A1 | 10/1989 |
| WO | 9100353 A2 | 1/1991 |
| WO | 9116422 A1 | 10/1991 |
| WO | 9200381 A1 | 1/1992 |
| WO | 9206154 A1 | 4/1992 |
| WO | 9219708 A1 | 11/1992 |
| WO | 9219709 A1 | 11/1992 |
| WO | 9219729 A1 | 11/1992 |
| WO | 9221760 A1 | 12/1992 |
| WO | 9324618 A1 | 12/1993 |
| WO | 9401541 A1 | 1/1994 |
| WO | 9402597 A1 | 2/1994 |
| WO | 9407998 A1 | 4/1994 |
| WO | 9425578 A1 | 11/1994 |
| WO | 9425583 A1 | 11/1994 |
| WO | 9500636 A1 | 1/1995 |
| WO | 9505249 A1 | 2/1995 |
| WO | 9506720 A1 | 3/1995 |
| WO | 9510602 A1 | 4/1995 |
| WO | 9510603 A1 | 4/1995 |
| WO | 9514783 A1 | 6/1995 |
| WO | 9522615 A1 | 8/1995 |
| WO | 9523221 A1 | 8/1995 |
| WO | 9524471 A1 | 9/1995 |
| WO | 9526397 A1 | 10/1995 |
| WO | 9530744 A2 | 11/1995 |
| WO | 9535381 A1 | 12/1995 |
| WO | 9535382 A2 | 12/1995 |
| WO | 9600292 A1 | 1/1996 |
| WO | 9605295 A2 | 2/1996 |
| WO | 9611262 A1 | 4/1996 |
| WO | 9612012 A1 | 4/1996 |
| WO | 9613580 A1 | 5/1996 |
| WO | 9623873 A1 | 8/1996 |
| WO | 9623874 A1 | 8/1996 |
| WO | 9627002 A1 | 9/1996 |
| WO | 9629397 A1 | 9/1996 |
| WO | 9630481 A | 10/1996 |
| WO | 9704079 A1 | 2/1997 |
| WO | 9707202 A1 | 2/1997 |
| WO | 9710342 A1 | 3/1997 |
| WO | 9741213 A1 | 11/1997 |
| WO | 9743424 A1 | 11/1997 |
| WO | 9808940 A1 | 3/1998 |
| WO | 9812307 A1 | 3/1998 |
| WO | 9820115 A1 | 5/1998 |
| WO | 9820116 A1 | 5/1998 |
| WO | 9826078 A1 | 6/1998 |
| WO | 9834946 A1 | 8/1998 |
| WO | 9901544 A1 | 1/1999 |
| WO | 9902702 A1 | 1/1999 |
| WO | 9909183 A1 | 2/1999 |
| WO | 9919467 A1 | 4/1999 |
| WO | 9923211 A1 | 5/1999 |
| WO | 9928448 A1 | 6/1999 |
| WO | 9929876 A2 | 6/1999 |
| WO | 9934011 A2 | 7/1999 |
| WO | 9942567 A1 | 8/1999 |
| WO | 9943793 A1 | 9/1999 |
| WO | 9943794 A1 | 9/1999 |
| WO | 9946399 A1 | 9/1999 |
| WO | 0004136 A1 | 1/2000 |
| WO | 0029560 A1 | 5/2000 |
| WO | 0060058 A2 | 10/2000 |
| WO | 0060059 A2 | 10/2000 |
| WO | 0060060 A2 | 10/2000 |
| WO | 0114532 A2 | 3/2001 |
| WO | 0114629 A1 | 3/2001 |
| WO | 0134784 A1 | 5/2001 |
| WO | 0134899 A1 | 5/2001 |
| WO | 0164852 A1 | 9/2001 |
| WO | 0166712 A2 | 9/2001 |
| WO | 0188107 A2 | 11/2001 |
| WO | 2001085888 A2 | 11/2001 |
| WO | 0196537 A2 | 12/2001 |
| WO | 0210355 A2 | 2/2002 |
| WO | 0231124 A2 | 4/2002 |
| WO | 02092797 A2 | 11/2002 |
| WO | 03014358 A2 | 2/2003 |
| WO | 2003089562 A1 | 10/2003 |
| WO | 2004113551 A1 | 12/2004 |
| WO | 2005001064 A2 | 1/2005 |
| WO | 2005003311 A1 | 1/2005 |
| WO | 2005018336 A1 | 3/2005 |
| WO | 2005019443 A2 | 3/2005 |
| WO | 2005056783 A1 | 6/2005 |
| WO | 2005066338 A1 | 7/2005 |
| WO | 2006007911 A1 | 1/2006 |
| WO | 200612902 A2 | 2/2006 |
| WO | 2006012899 A1 | 2/2006 |
| WO | 2006031554 A2 | 3/2006 |
| WO | 2006045391 A1 | 5/2006 |
| WO | 2006063594 A1 | 6/2006 |
| WO | 2006066596 A2 | 6/2006 |
| WO | 2006136161 A2 | 12/2006 |
| WO | 2007044993 A2 | 4/2007 |
| WO | 2008000567 A1 | 1/2008 |
| WO | 2008000825 A1 | 1/2008 |
| WO | 2008087426 A1 | 7/2008 |
| WO | 2008088493 A2 | 7/2008 |
| WO | 2008092919 A1 | 8/2008 |
| WO | 2008101894 A1 | 8/2008 |
| WO | 2009061381 A2 | 5/2009 |
| WO | 2009098659 A1 | 8/2009 |
| WO | 2009098660 A1 | 8/2009 |
| WO | 2009100102 A2 | 8/2009 |
| WO | 2009112992 A1 | 9/2009 |
| WO | 2009124160 A1 | 10/2009 |
| WO | 2009140504 A1 | 11/2009 |
| WO | 2009149144 A2 | 12/2009 |
| WO | 2009149145 A2 | 12/2009 |
| WO | 2009149200 A2 | 12/2009 |
| WO | 2009149419 A2 | 12/2009 |
| WO | 2009152031 A1 | 12/2009 |
| WO | 2010056640 A2 | 5/2010 |
| WO | 2010056653 A2 | 5/2010 |
| WO | 2010059413 A2 | 5/2010 |
| WO | 2010059483 A1 | 5/2010 |
| WO | 2010088112 A1 | 8/2010 |
| WO | 2010088447 A1 | 8/2010 |
| WO | 2010090915 A1 | 8/2010 |
| WO | 2010091221 A1 | 8/2010 |
| WO | 2010104675 A1 | 9/2010 |
| WO | 2010115021 A2 | 10/2010 |
| WO | 2010116139 A1 | 10/2010 |
| WO | 2010117511 A1 | 10/2010 |
| WO | 2010135238 A1 | 11/2010 |
| WO | 2011072099 A2 | 6/2011 |
| WO | 2011076123 A1 | 6/2011 |
| WO | 2011076997 A1 | 6/2011 |
| WO | 2011080352 A1 | 7/2011 |
| WO | 2011080353 A1 | 7/2011 |
| WO | 2011080354 A1 | 7/2011 |
| WO | 2011082429 A1 | 7/2011 |
| WO | 2011087836 A2 | 7/2011 |
| WO | 2011094687 A1 | 8/2011 |
| WO | 2011094690 A1 | 8/2011 |

(56) References Cited

FOREIGN PATENT DOCUMENTS

| WO | 2011098531 | A1 | 8/2011 |
|---|---|---|---|
| WO | 2011082425 | A2 | 9/2011 |
| WO | 2011127102 | A1 | 10/2011 |
| WO | 2011140364 | A1 | 11/2011 |
| WO | 2011153516 | A2 | 12/2011 |
| WO | 2011163428 | A1 | 12/2011 |
| WO | 2012027404 | A1 | 3/2012 |
| WO | 2012059336 | A1 | 5/2012 |
| WO | 2012104613 | A1 | 8/2012 |
| WO | 2012151534 | A1 | 11/2012 |
| WO | 2013063460 | A2 | 5/2013 |
| WO | 2013184577 | A1 | 12/2013 |
| WO | 2014007921 | A1 | 1/2014 |
| WO | 2014164777 | A1 | 10/2014 |
| WO | 2014164800 | A1 | 10/2014 |
| WO | 2014164834 | A1 | 10/2014 |
| WO | 2015050723 | A1 | 4/2015 |
| WO | 2015077126 | A1 | 5/2015 |

OTHER PUBLICATIONS

Sumitani et al., New type of starch-binding domain: the direct repeat motif in C-terminal region of *Bacillus* sp. 195 α-amylase contributes to starch binding and raw starch degrading, Biochem. J., 2000, vol. 350, pp. 477-484.

PCT International Search Report and Written Opinion of the International Searching Authority for International Application No. PCT/US2016/066031; ISA/EPO dated Jun. 1, 2017.

Christophersen et al., Enzymatic Characterisation of Novamyl®, a Thermostable α-amylase, Starch 1998, vol. 50, pp. 39-45.

Uniprot Database, Accession No. A0A0C2W9X1, Nov. 2015, 2 pages.

\* cited by examiner

ALPHA-AMYLASE COMBINATORIAL VARIANTS

CROSS-REFERENCE TO RELATED APPLICATIONS

The present application claims the benefit of U.S. Provisional Application No. 62/265,301, filed Dec. 9, 2015, which is hereby incorporated by reference in its entirety.

FIELD OF THE INVENTION

Disclosed are compositions and methods relating to variant α-amylases containing a plurality of combinable mutations. The variant α-amylases are useful, for example, for starch liquefaction and saccharification, cleaning starchy stains, textile desizing, baking, and brewing.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) gelatinization and liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup. The resulting syrup also may be fermented with microorganisms, such as yeast, to produce commercial products including ethanol, citric acid, lactic acid, succinic acid, itaconic acid, monosodium glutamate, gluconates, lysine, other organic acids, other amino acids, and other biochemicals, for example. Fermentation and saccharification can be conducted simultaneously (i.e., an SSF process) to achieve greater economy and efficiency.

α-amylases hydrolyze starch, glycogen, and related polysaccharides by cleaving internal α-1,4-glucosidic bonds at random. α-amylases, particularly from Bacilli, have been used for a variety of different purposes, including starch liquefaction and saccharification, textile desizing, starch modification in the paper and pulp industry, brewing, baking, production of syrups for the food industry, production of feedstocks for fermentation processes, and in animal feed to increase digestability. These enzymes can also be used to remove starchy soils and stains during dishwashing and laundry washing.

Numerous publications have described mutations in α-amylases. However, not all mutations produce the same effect in different molecules and not all mutation can be combined. In addition, many mutations produce molecules that have certain desirable qualities at the expense of other properties. The need exists for robust engineered α-amylases molecules.

SUMMARY

The present compositions and methods relate to variant amylase polypeptides, and methods of use, thereof. Aspects and embodiments of the present compositions and methods are summarized in the following separately-numbered paragraphs:

1. In a first aspect, a recombinant variant of a parent α-amylase is provided, comprising: a mutation at an amino acid residue corresponding to R375, and optionally S360; and at least one mutation, and optionally at least two mutations, at an amino acid residue, or residues, corresponding to an amino acid residue selected from the group consisting of N126, F153, T180, E187, and I203; wherein the variant α-amylase or the parent α-amylase has at least 60%, optionally 70%, optionally 80%, optionally 85%, optionally 90%, or optionally 95%, amino acid sequence identity relative to SEQ ID NO: 1, which is used for numbering; and wherein the variant has increased low pH stability and/or starch liquefaction activity, compared to the parent α-amylase or a reference α-amylase differing from the variant α-amylase only by the absence of the mutations.

2. In some embodiments, the variant α-amylase of paragraph 1 comprises the mutation R375Y, and optionally S360A; and at least one mutation, and optionally at least two mutations, at an amino acid residue, or residues, corresponding to an amino acid residue selected from the group consisting of N126Y, F153W, T180H, T180D, E187P, and I203Y, using SEQ ID NO: 1 for numbering. In particular embodiments, the variant α-amylase of paragraph 1 specifically does not include a mutation at position F153.

3. In some embodiments, the variant α-amylase of paragraph 1 or 2 comprises the mutations R375Y and S360A, using SEQ ID NO: 1 for numbering.

4. In some embodiments, the variant α-amylase of paragraph 3 further comprises the mutations N126Y, F153W, T180H, and E187P, using SEQ ID NO: 1 for numbering.

5. In some embodiments, the variant α-amylase of any of the preceding paragraphs, further comprises a mutation as a position selected from the group consisting of A275, T89, S92 and Y301, using SEQ ID NO: 1 for numbering. In particular embodiments, the specific mutations are A275D or A275E, T89E, S92R, and/or Y301A.

6. In some embodiments, the variant α-amylase of any of the preceding paragraphs further comprises a deletion of at least one amino acid residue corresponding to R178, G179, T180, and G181, using SEQ ID NO: 1 for numbering.

7. In some embodiments, the variant α-amylase of any of the preceding paragraphs further comprises deletions of amino acid residues corresponding to R178 and G179, or T180 and G181, using SEQ ID NO: 1 for numbering.

8. In some embodiments, the variant α-amylase of any of the preceding paragraphs further comprises a mutation at an amino acid residue corresponding to G476, G477, E132, Q167, A277, R458, T459, and/or D460, using SEQ ID NO: 1 for numbering.

9. In some embodiments, the variant α-amylase of any of the preceding paragraphs is from a *Cytophaga* species or not from a *Bacillus* species.

10. In another aspect, a method for converting starch to oligosaccharides is provided, comprising contacting starch with effective amount of the variant amylase of any of the paragraphs 1-9.

11. In another aspect, a composition for liquefying starch comprising the variant amylase of any of paragraphs 1-9 is provided.

12. In another aspect, a recombinant variant of a parent α-amylase is provided, comprising: a mutation at at least one, and optionally a plurality, of amino acid residues corresponding to position T38, N126, F153, E187, I203, G476, and G477; and, optionally at least one mutation at an amino acid residue corresponding to R178, G179, T180, and G181, wherein the variant α-amylase or the parent α-amylase has at least 60%, optionally 70%, optionally 80%, optionally 85%, optionally 90%, or optionally 95%, amino acid sequence identity relative to SEQ ID NO: 1, which is used for numbering; and wherein the variant has increased detergent stability and/or cleaning performance compared to the parent α-amylase or a reference α-amylase differing from the variant α-amylase only by the absence of the mutations.

13. In some embodiments, the variant α-amylase of paragraph 12 comprises at least one, and optionally a plurality, of the mutations T38N, N126Y, F153W, E187P, I203Y, G476K, and G477E, using SEQ ID NO: 1 for numbering. In particular embodiments, the variant α-amylase of paragraph 12 specifically does not include a mutation at position F153.

14. In some embodiments, the variant α-amylase of paragraphs 12 or 13 further comprises a mutation at position T129, using SEQ ID NO: 1 for numbering.

15. In some embodiments, the variant α-amylase of paragraph 14 further comprises the mutation T129I, using SEQ ID NO: 1 for numbering.

16. In some embodiments, the variant α-amylase of any of paragraphs 12-15 further comprises deletions of amino acid residues corresponding to R178 and G179, or T180 and G181, using SEQ ID NO: 1 for numbering.

17. In some embodiments, the variant α-amylase of any of paragraphs 12-16 further comprises a mutation at an amino acid residue corresponding to E132, Q167, A277, R458, T459, and/or D460, using SEQ ID NO: 1 for numbering.

18. In some embodiments, the variant α-amylase of any of paragraphs 12-17 lacks a mutation at an amino acid residue corresponding to position N88, N134, and/or L171, using SEQ ID NO: 1 for numbering.

19. In some embodiments, the variant α-amylase of any of paragraphs 12-18 is from a *Cytophaga* species or not from a *Bacillus* species.

20. In another aspect, a method for removing a starchy stain or soil from a surface is provided, comprising contacting the surface with an effective amount of the variant amylase of any of the paragraphs 12-19, and allowing the polypeptide to hydrolyze starch components present in the starchy stain to produce smaller starch-derived molecules that dissolve in the aqueous composition, thereby removing the starchy stain from the surface.

21. In another aspect, a detergent composition comprising the variant amylase of any of paragraphs 12-20 is provided.

These and other aspects and embodiments of the compositions and methods will be apparent from the present description and drawings.

DETAILED DESCRIPTION

Figure 1:
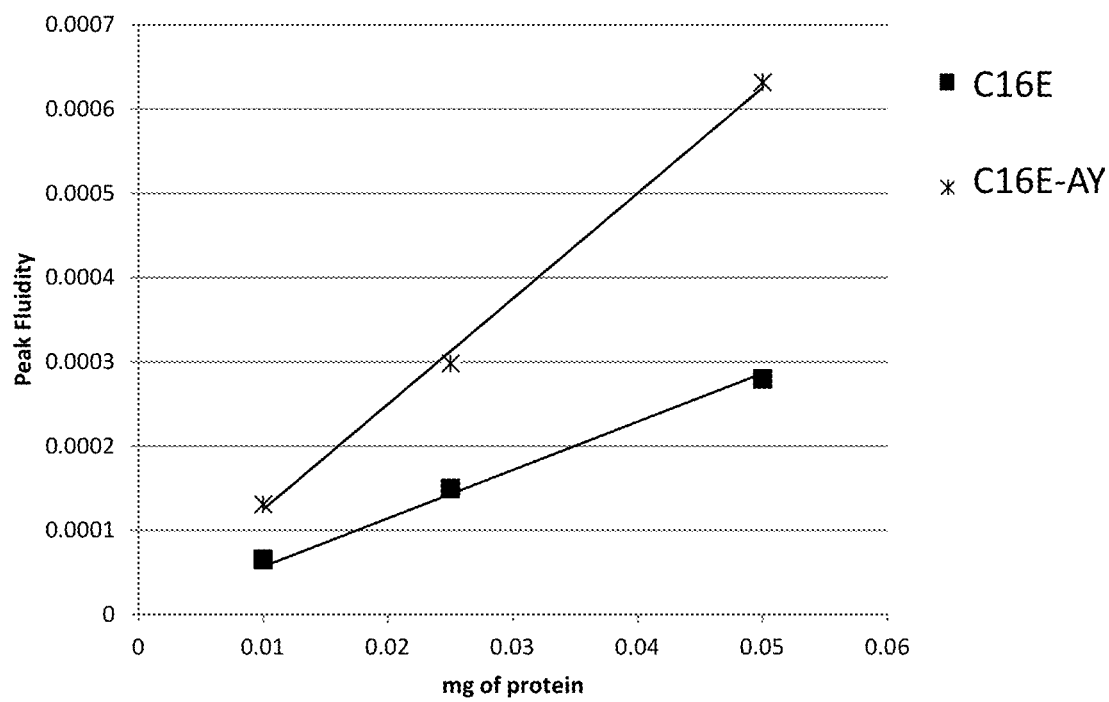
FIG. 1 is a graph showing peak fluidity values per mg enzyme resulting from incubation of a starch substrate with α-amylase variants C16E and C16E-AY.

Described are compositions and methods relating to variant α-amylase enzymes. Exemplary applications for the variant amylase enzymes are for starch liquefaction and saccharification, for cleaning starchy stains in laundry, dishwashing, and other applications, for textile processing (e.g., desizing), in animal feed for improving digestibility, and and for baking and brewing. These and other aspects of the compositions and methods are described in detail, below.

Prior to describing the various aspects and embodiments of the present compositions and methods, the following definitions and abbreviations are described.

1. Definitions and Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art. The following terms are provided below.

1.1. Abbreviations and Acronyms

The following abbreviations/acronyms have the following meanings unless otherwise specified:

ABTS   2,2-azino-bis-3-ethylbenzothiazoline-6-sulfonic acid
AE or AEO alcohol ethoxylate
AES or AEOS alcohol ethoxysulfate
AkAA *Aspergillus kawachii* α-amylase
AnGA *Aspergillus niger* glucoamylase
AOS α-olefinsulfonate
AS alkyl sulfate
cDNA complementary DNA
ct/kg cents/kg (US currency)
CMC carboxymethylcellulose
DE dextrose equivalent
DNA deoxyribonucleic acid
DPn degree of saccharide polymerization having n subunits
ds or DS dry solids
DTMPA diethylenetriaminepentaacetic acid
EC Enzyme Commission
EDTA ethylenediaminetetraacetic acid
EO ethylene oxide (polymer fragment)
EOF end of fermentation
FH French hardness
GA glucoamylase
GAU/g ds glucoamylase activity unit/gram dry solids GH general hardness
HDL high density liquid detergent
HDD heavy duty powder detergent
HSG high suds granular detergent
HFCS high fructose corn syrup
HgGA *Humicola grisea* glucoamylase
IPTG isopropyl β-D-thiogalactoside
IRS insoluble residual starch
kDa kiloDalton
LAS linear alkylbenzenesulfonate
LAT, BLA *B. licheniformis* amylase
MW molecular weight
MWU modified Wohlgemuth unit; $1.6 \times 10^{-5}$ mg/MWU=unit of activity
NCBI National Center for Biotechnology Information
NOBS nonanoyloxybenzenesulfonate
NTA nitriloacetic acid
OxAm Purastar HPAM 5000L (Danisco US Inc.)
PAHBAH p-hydroxybenzoic acid hydrazide
PEG polyethyleneglycol
pI isoelectric point
PI performance index
ppm parts per million, e.g., μg protein per gram dry solid
PVA poly(vinyl alcohol)
PVP poly(vinylpyrrolidone)
RCF relative centrifugal/centripetal force (i.e., x gravity)
RNA ribonucleic acid
SAS alkanesulfonate
SDS-PAGE sodium dodecyl sulfate polyacrylamide gel electrophoresis
SSF simultaneous saccharification and fermentation
SSU/g solid soluble starch unit/gram dry solids
sp. species
TAED tetraacetylethylenediamine
Tm melting temperature
TrGA *Trichoderma reesei* glucoamylase
w/v weight/volume
w/w weight/weight
v/v volume/volume
wt % weight percent
° C. degrees Centigrade
H$_2$O water
dH$_2$O or DI deionized water
dIH$_2$O deionized water, Milli-Q filtration
g or gm grams
μg micrograms
mg milligrams
kg kilograms
μL and μl microliters
mL and ml milliliters
mm millimeters
μm micrometer
M molar
mM millimolar
μM micromolar
U units
sec seconds
min(s) minute/minutes
hr(s) hour/hours
DO dissolved oxygen
Ncm Newton centimeter
ETOH ethanol
eq. equivalents
N normal
uPWA variant α-amylase derived from *Pyrococcus woesei*
PWA α-amylase from *Pyrococcus woesei*
MWCO molecular weight cut-off
SSRL Stanford Synchrotron Radiation Lightsource
PDB Protein Database
CAZy Carbohydrate-Active Enzymes database
Tris-HCl tris(hydroxymethyl)aminomethane hydrochloride
HEPES 4-(2-hydroxyethyl)-1-piperazineethanesulfonic acid

1.2. Definitions

The terms "amylase" or "amylolytic enzyme" refer to an enzyme that is, among other things, capable of catalyzing the degradation of starch. α-amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) 0-glycosidic linkages within the starch molecule in a random fashion yielding polysaccharides containing three or more (1-4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

The term "starch" refers to any material comprised of the complex polysaccharide carbohydrates of plants, comprised of amylose and amylopectin with the formula (C6H10O5)x, wherein X can be any number. The term includes plant-based materials such as grains, cereal, grasses, tubers and roots, and more specifically materials obtained from wheat, barley, corn, rye, rice, sorghum, brans, cassava, millet, milo, potato, sweet potato, and tapioca. The term "starch" includes granular starch. The term "granular starch" refers to raw, i.e., uncooked starch, e.g., starch that has not been subject to gelatinization.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

In the case of the present α-amylases, "activity" refers to α-amylase activity, which can be measured as described, herein.

The term "performance benefit" refers to an improvement in a desirable property of a molecule. Exemplary performance benefits include, but are not limited to, increased hydrolysis of a starch substrate, increased grain, cereal or other starch substrate liquefaction performance, increased cleaning performance, increased thermal stability, increased detergent stability, increased storage stability, increased solubility, an altered pH profile, decreased calcium dependence, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

The terms "protease" and "proteinase" refer to an enzyme protein that has the ability to perform "proteolysis" or "proteolytic cleavage" which refers to hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity (See e.g., Kalisz, "Microbial Proteinases," In: Fiechter (ed.), *Advances in Biochemical Engineering/Biotechnology*, (1988)). For example, proteolytic activity may be ascertained by comparative assays which analyze the respective protease's ability to hydrolyze a commercial substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450, both of which are incorporated herein by reference). The pNA assay (See e.g., Del Mar et al., Anal. Biochem. 99:316-320 [1979]) also finds use in determining the active enzyme concentration for fractions collected during gradient elution. This assay measures the rate at which p-nitroaniline is released as the enzyme hydrolyzes a soluble synthetic peptide substrate, such as succinyl-alanine-alanine-proline-phenylalanine-p-nitroanilide (suc-AAPF-pNA), and cleavage occurs between the C-terminal amino acid (phenylalanine) and the p-NA, causing the production of yellow color from the hydrolysis reaction, which is measured at 410 nm on a spectrophotometer and is proportional to the active enzyme concentration. Measurement of the color change allows calculation of the rate of the reaction. In addition, absorbance measurements at 280 nanometers (nm) can be used to determine the total protein concentration. The active enzyme/total protein ratio gives the enzyme purity when a reference standard is used.

The terms "serine protease" refers to enzymes that cleave peptide bonds in proteins, in which enzymes serine serves as the nucleophilic amino acid at the enzyme active site. Serine proteases fall into two broad categories based on their structure: chymotrypsin-like (trypsin-like) or subtilisin-like. Most commonly used in laundry and dishwashing detergents are serine protease, particularly subtlisins.

The term "TIM barrel" refers to a three dimensional polypeptide structure that include eight α-helices and eight parallel β-strands that alternate along the peptide backbone.

The term "surface-exposed" with respect to an amino acid residue in a polypeptide refers to a residue that is on the exterior surface of a polypeptide when the polypeptide is intact and properly folded, i.e., not denatured or fragmented. In the case of an α-amylase, the structure is referred to as a TIM barrel.

The term "non-canonical" with reference to an amino acid residue in a polypeptide refers to a residue that is not normally found at a given position based on amino acid sequence alignments of similar molecules using Clustal W with default parameter. In some cases, the particular residue is found at a given position in only 1 in 10, 1 in 20, 1 in 30, 1 in 50, or even 1 in 100 similar molecules.

"Combinatorial variants" are variants comprising two or more mutations, e.g., 2, 3, 4, 5, 6, 7, 8, 9, 10, or more, substitutions, deletions, and/or insertions.

"Combinable mutations" are mutations at any amino acid position that can be used to make combinatorial variants. Combinable mutations improve at least one desired property of the molecule (in this case, an amylase), while not significantly decreasing either expression, activity, or stability.

Terms, such as "a remaining non-G residue in the calcium-binding loop," "a non-G amino acid residue remaining in the calcium-binding loop," and similar terms, refer to an amino acid residue in the calcium-binding loop of a variant α-amylase, which remains in the variant following a deletion of at least one amino acid residue in the calcium-binding loop of a parent α-amylases, and which is not a glycine residue. The non-G residue may be a member of an "XG" pair, of which there are two in most α-amylases, and may be the remaining non-G residue following a pair-wise deletion of one of the two XG residue pairs in the calcium binding loop of a parent α-amylase.

A "stabilizing interaction" between the residue at position 132 (using SEQ ID NO: 1 for numbering) and the remaining non-G residue in the $X_1G/S_1X_2G_2$ motif (corresponding to residues at positions 178-181 of SEQ ID NO: 1) refers to a hydrogen bond or a salt bridge formed between the side chains of the subject amino acid residues. The stabilization can result from charge balancing the interacting residues, such that if one residue is positively charged at a preselected pH, the other is negatively charged, and the overall charge is zero.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an amylase is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptides, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t\frac{1}{2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may contain chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na3 citrate, pH 7.0). Hybridized, duplex nucleic acids are characterized by a melting temperature (Tm), where one half of the hybridized nucleic acids are unpaired with the complementary strand. Mismatched nucleotides within the duplex lower the Tm. A nucleic acid encoding a variant α-amylase may have a Tm reduced by 1° C.-3° C. or more compared to a duplex formed between the nucleotide of SEQ ID NO: 2 and its identical complement.

A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein.

As used herein, "water hardness" is a measure of the minerals (e.g., calcium and magnesium) present in water.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

"A cultured cell material comprising an amylase" or similar language, refers to a cell lysate or supernatant (including media) that includes an amylase as a component. The cell material may be from a heterologous host that is grown in culture for the purpose of producing the amylase.

"Percent sequence identity" means that a particular sequence has at least a certain percentage of amino acid residues identical to those in a specified reference sequence, when aligned using the CLUSTAL W algorithm with default parameters. See Thompson et al. (1994) Nucleic Acids Res. 22:4673-4680. Default parameters for the CLUSTAL W algorithm are:
  Gap opening penalty: 10.0
  Gap extension penalty: 0.05
  Protein weight matrix: BLOSUM series
  DNA weight matrix: IUB
  Delay divergent sequences %: 40
  Gap separation distance: 8
  DNA transitions weight: 0.50
  List hydrophilic residues: GPSNDQEKR
  Use negative matrix: OFF
  Toggle Residue specific penalties: ON
  Toggle hydrophilic penalties: ON
  Toggle end gap separation penalty OFF.

Deletions are counted as non-identical residues, compared to a reference sequence. Deletions occurring at either termini are included. For example, a variant with five amino acid deletions of the C-terminus of the mature CspAmy2 polypeptide of SEQ ID NO: 1 would have a percent sequence identity of 99% (612/617 identical residues×100, rounded to the nearest whole number) relative to the mature polypeptide. Such a variant would be encompassed by a variant having "at least 99% sequence identity" to a mature amylase polypeptide.

"Fused" polypeptide sequences are connected, i.e., operably linked, via a peptide bond between two subject polypeptide sequences.

The term "filamentous fungi" refers to all filamentous forms of the subdivision Eumycotina, particularly *Pezizomycotina* species.

The term "degree of polymerization" (DP) refers to the number (n) of anhydro-glucopyranose units in a given saccharide. Examples of DP1 are the monosaccharides glucose and fructose. Examples of DP2 are the disaccharides maltose and sucrose. The term "DE," or "dextrose equivalent," is defined as the percentage of reducing sugar, i.e., D-glucose, as a fraction of total carbohydrate in a syrup.

The term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

An "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or fungal fermentation. "Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, India pale ale, lager, pilsner, bitter, Happoshu (second beer), third beer, dry beer, near beer, light beer, low alcohol beer, low calorie beer, porter, bock, dopplebock, stout, porter, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material that is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

"Iodine-positive starch" or "IPS" refers to (1) amylose that is not hydrolyzed after liquefaction and saccharification, or (2) a retrograded starch polymer. When saccharified starch or saccharide liquor is tested with iodine, the high DPn amylose or the retrograded starch polymer binds iodine and produces a characteristic blue color. The saccharide liquor is thus termed "iodine-positive saccharide," "blue saccharide," or "blue sac."

The terms "retrograded starch" or "starch retrogradation" refer to changes that occur spontaneously in a starch paste or gel on ageing.

The term "about" refers to ±15% to the referenced value.

2. α-Amylase Variants

An aspect of the present compositions and methods are variant α-amylase enzymes that include combinations of mutations that improve their performance in industrial applications. The combinatorial variants were initially discovered using an α-amylase from *Cytophaga* sp. (herein, "CspAmy2 amylase"), which was previously described by Jeang, C-L et al. ((2002) *Applied and Environmental Microbiology*, 68:3651-54). The amino acid sequence of the mature form of the CspAmy2 α-amylase polypeptide is shown below as SEQ ID NO: 1:

```
AATNGTMMQY FEWYVPNDGQ QWNRLRTDAP YLSSVGITAV
WTPPAYKGTS QADVGYGPYD LYDLGEFNQK GTVRTKYGTK
GELKSAVNTL HSNGIQVYGD VVMNHKAGAD YTENVTAVEV
NPSNRNQETS GEYNIQAWTG FNFPGRGTTY SNFKWQWFHF
DGTDWDQSRS LSRIFKFRGT GKAWDWEVSS ENGNYDYLMY
ADIDYDHPDV VNEMKKWGVW YANEVGLDGY RLDAVKHIKF
SFLKDWVDNA RAATGKEMFT VGEYWQNDLG ALNNYLAKVN
YNQSLFDAPL HYNFYAASTG GGYYDMRNIL NNTLVASNPT
KAVTLVENHD TQPGQSLEST VQPWFKPLAY AFILTRSGGY
PSVFYGDMYG TKGTTTREIP ALKSKIEPLL KARKDYAYGT
QRDYIDNPDV IGWTREGDST KAKSGLATVI TDGPGGSKRM
YVGTSNAGEI WYDLTGNRTD KITIGSDGYA TFPVNGGSVS
VWVQQ
```

In SEQ ID NO: 1, R178 and G179, are underlined. A variant of the *Cytophaga* sp. α-amylase having a deletion of both R178 and G179 (herein, "CspAmy2-v1") has also been described (Shiau, R-J. et al. (2003) *Applied and Environmental Microbiology*, 69:2383-85). The amino acid sequence of the mature CspAmy2-v1 a-amylase polypeptide is shown below as SEQ ID NO: 2:

```
AATNGTMMQY FEWYVPNDGQ QWNRLRTDAP YLSSVGITAV
WTPPAYKGTS QADVGYGPYD LYDLGEFNQK GTVRTKYGTK
GELKSAVNTL HSNGIQVYGD VVMNHKAGAD YTENVTAVEV
NPSNRNQETS GEYNIQAWTG FNFPGRGTTY SNFKWQWFHF
DGTDWDQSRS LSRIFKFTGK AWDWEVSSEN GNYDYLMYAD
IDYDHPDVVN EMKKWGVWYA NEVGLDGYRL DAVKHIKFSF
LKDWVDNARA ATGKEMFTVG EYWQNDLGAL NNYLAKVNYN
QSLFDAPLHY NFYAASTGGG YYDMRNILNN TLVASNPTKA
VTLVENHDTQ PGQSLESTVQ PWFKPLAYAF ILTRSGGYPS
VFYGDMYGTK GTTTREIPAL KSKIEPLLKA RKDYAYGTQR
DYIDNPDVIG WTREGDSTKA KSGLATVITD GPGGSKRMYV
GTSNAGEIWY DLTGNRTDKI TIGSDGYATF PVNGGSVSVW
VQQ
```

Using SEQ ID NO: 2 as a starting point, a number of combinatorial CspAmy2 variants were previously made and tested (see, e.g., WO/2014/164777, which is incorporated by reference). The best performing variants generally included a stabilizing mutation at an amino acid position corresponding to either E187 or S241, along with additional mutations that improved desirable properties.

Described herein are further improved variants of CspAmy2, which are tailored to provide a high level of performance in selected applications. All embodiments of the present compositions and methods are described with reference to SEQ ID NO: 1 for numbering; however, the compositions and methods are not limited to CspAmy2 variants.

In some embodiments, the present compositions and methods include variant recombinant α-amylases having a mutation at an amino acid residue corresponding to R375, and optionally at an amino acid residue corresponding to S360; in combination with one, a plurality, or all, of the previously identified mutations at positions N126, F153, T180, E187, and I203. A mutation at position S241 (particularly S241Q or S241A) is expected to substitute for the mutation at position E187 but the two mutations should not be combined.

In some embodiments, the variant α-amylase includes the mutation R375Y, and optionally S360A; and at least one mutation, and optionally at least two mutations, a plurality of mutations, or all mutations, at an amino acid residue, or residues, corresponding to the group consisting of N126Y, F153W, T180H, T180D, E187P, and I203Y. In a particular embodiment, the variant α-amylase includes both the mutations R375Y and S360A.

In some embodiments, the variant α-amylase further includes one or more previously described mutations at an amino acid residue corresponding to G476, G477, E132, Q167, A277, R458, T459, and/or D460.

In some embodiments, the variant has increased low pH stability and/or starch liquefaction activity, compared to the parent α-amylase, or reference α-amylase, differing from the variant α-amylase only by the absence of the mutations.

In some embodiments, the recombinant variant of a parent α-amylase includes mutations at at least one, a plurality, or even all of the amino acid residues corresponding to positions T38, N126, F153, E187, I203, G476, and G477. As above, a mutation at position S241 (particularly S241Q or S241A) is expected to substitute for the mutation at position E187 but the two mutation should not be combined. In particular embodiments, the variant α-amylase includes at least one, a plurality, or even all the mutations T38N, N126Y, F153W, E187P, I203Y, G476K, and G477E. In some embodiments, the variant further includes a mutation at position T129. In a particular embodiment, the mutation is T129I.

In some embodiments, the variant α-amylase further includes one or more previously described mutations at an amino acid residue corresponding to G476, G477, E132, Q167, A277, R458, T459, and/or D460.

In some embodiments, the variant specifically lacks a mutation at one, two, or all the amino acid residues corresponding to positions N88, N134, and/or L171.

In some embodiments, the variant has increased detergent stability and/or cleaning performance compared to the parent α-amylase, or a reference α-amylase differing from the variant α-amylase only by the absence of the mutations.

In some embodiments, any of the aforementioned variant α-amylases further include a deletion in the $X_1G/S_1X_2G_2$ motif adjacent to the calcium-binding loop corresponding to R178, G179, T180, and G181, using SEQ ID NO: 1 for numbering. In some embodiments, the variant a-amylases include adjacent, pair-wise deletions of amino acid residues corresponding to R178 and G179, or T180 and G181. A deletion in amino acid residues corresponding to R178 and G179 may be referred to as "ΔRG," while a deletion in amino acid residues corresponding to T180 and G181 may be referred to as "ΔTG." This nomenclature will naturally change depending on the amino acid residues originally present in the parent molecule.

Exemplary combinations of mutation (using SEQ ID NO: 1 for numbering) are shown, below:

N126Y+F153W+T180H+E187P+I203Y+R375Y
N126Y+F153W+T180H+E187P+I203Y+S360A+R375Y
T38N+N126Y+F153W+T180D+E187P+I203Y+
  G476K+G477E
T38N+N126Y+T129I+F153W+T180D+E187P+I203Y+
  G476K+G477E

All the above combinations of mutation are contemplated for use in conjunction with the aforementioned deletions at positions corresponding to R178, G179, T180, and/or G181. Such deletions may be naturally occurring, as in the case of *Bacillus licheniformis* α-amylase.

It is known that many bacterial (and other) α-amylases share the same fold, often share significant amino acid sequence identity, and sometimes benefit from the same mutations; therefore, the mutations are expected to be transferable to other parental amylases. Corresponding amino acid positions in other α-amylases be identified by amino acid sequence alignment using CspAmy2 (SEQ ID NO: 1) using Clustal W with default parameters. α-amylases in which the foregoing mutations are likely to produce a performance benefit include those having a similar fold and/or having 60% or greater amino acid sequence identity to any of the well-known *Bacillus* amylases (e.g., from *B. licheniformis* (i.e., BLA and LAT), *B. stearothermophilus* (i.e., BSG), and *B. amyloliquefaciens* (i.e., P00692, BACAM, and BAA)), Carbohydrate-Active Enzymes database (CAZy) Family 13 amylases, or any amylase that has heretofore been referred to by the descriptive term, "Termamyl-like." Exemplary α-amylases include but are not limited to those from *Bacillus* sp. SG-1, *Bacillus* sp. 707, *Bacillus* sp. DSM12368 (i.e., A7-7), *Bacillus* sp. DSM 12649 (i.e., AA560), *Bacillus* sp. SP722, *Bacillus megaterium* (DSM90 14), and KSM AP1378.

The reader will appreciate that where an α-amylase naturally has a mutation listed above (i.e., where the wild-type α-amylase already comprised a residue identified as a mutation), then that particular mutation does not apply to that α-amylase. However, other described mutations may work in combination with the naturally occurring residue at that position.

In some embodiments, the present α-amylase variants have the indicated combinations of mutations and a defined degree of amino acid sequence homology/identity to SEQ ID NO: 1, for example, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence homology/identity.

In some embodiments, the present α-amylase variants have the indicated combinations of mutations and are derived from a parental amylase having a defined degree of amino acid sequence homology/identity to SEQ ID NO: 1, for example, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence homology/identity.

Furthermore, the present amylases may include any number of conservative amino acid substitutions. Exemplary conservative amino acid substitutions are listed in Table 1

TABLE 1

Conservative amino acid substitutions

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The reader will appreciate that some of the above mentioned conservative mutations can be produced by genetic manipulation, while others are produced by introducing synthetic amino acids into a polypeptide by genetic or other means.

The present amylase may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective amylase polypeptides. The present amylase polypeptides may also be truncated to remove the N or C-termini, so long as the resulting polypeptides retain amylase activity.

The present amylase may be a "chimeric" or "hybrid" polypeptide, in that it includes at least a portion of a first amylase polypeptide, and at least a portion of a second amylase polypeptide (such chimeric amylases have recently been "rediscovered" as domain-swap amylases). The present amylases may further include heterologous signal sequence, an epitope to allow tracking or purification, or the like. Exemplary heterologous signal sequences are from *B. licheniformis* amylase (LAT), *B. subtilis* (AmyE or AprE), and *Streptomyces* CelA.

2.5. Nucleotides Encoding Variant Amylase Polypeptides

In another aspect, nucleic acids encoding a variant amylase polypeptide are provided. The nucleic acid may encode a particular amylase polypeptide, or an amylase having a specified degree of amino acid sequence identity to the particular amylase.

In one example, the nucleic acid encodes an amylase having at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1 (excluding the portion of the nucleic acid that encodes the signal sequence). It will be appreciated that due to the degeneracy of the genetic code, a plurality of nucleic acids may encode the same polypeptide.

In another example, the nucleic acid hybridizes under stringent or very stringent conditions to a nucleic acid encoding (or complementary to a nucleic acid encoding) an amylase having at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1 (excluding the portion of the nucleic acid that encodes the signal sequence).

In some embodiments, the nucleic acid hybridizes under stringent or very stringent conditions to the nucleic acid of SEQ ID NO: 7, or to a nucleic acid complementary to this nucleic acids.

Nucleic acids may encode a "full-length" ("fl" or "FL") amylase, which includes a signal sequence, only the mature form of an amylase, which lacks the signal sequence, or a truncated form of an amylase, which lacks the N or C-terminus of the mature form.

A nucleic acid that encodes a α-amylase can be operably linked to various promoters and regulators in a vector suitable for expressing the α-amylase in host cells. Exemplary promoters are from *B. licheniformis* amylase (LAT), *B. subtilis* (AmyE or AprE), and *Streptomyces* CelA. Such a nucleic acid can also be linked to other coding sequences, e.g., to encode a chimeric polypeptide.

3. Production of Variant Amylases

The present variant amylases can be produced in host cells, for example, by secretion or intracellular expression, using methods well-known in the art. Suitable assays can be used to monitor amylase activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. α-amylase activity also may be measured by any known method, such as the PAHBAH or ABTS assays, described below.

Fermentation, separation, and concentration techniques are well known in the art and conventional methods can be used to prepare a concentrated, variant-α-amylase-polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultra-filtration, extraction, or chromatography, or the like, are generally used.

It is desirable to concentrate a variant α-amylase polypeptide-containing solution in order to optimize recovery. Use of unconcentrated solutions requires increased incubation time in order to collect the enriched or purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of enrichment and purification include but are not limited to rotary vacuum filtration and/or ultrafiltration.

The enzyme solution is concentrated into a concentrated enzyme solution until the enzyme activity of the concentrated variant α-amylase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate an amylase. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific variant α-amylase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, variant amylase concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be enriched or purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain an enriched or purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of enriched or purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the enriched or purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water. For example, the enriched or purified enzyme precipitate is washed with water containing the metal halide precipitation agent, or with water containing the metal halide and the organic compound precipitation agents.

During fermentation, a variant α-amylase polypeptide accumulates in the culture broth. For the isolation, enrichment, or purification of the desired variant α-amylase, the culture broth is centrifuged or filtered to eliminate cells, and the resulting cell-free liquid is used for enzyme enrichment or purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further enrichment or purification, a conventional procedure such as ion exchange chromatography may be used.

Enriched or purified enzymes are useful for laundry and cleaning applications. For example, they can be used in laundry detergents and spot removers. They can be made into a final product that is either liquid (solution, slurry) or solid (granular, powder).

A more specific example of enrichment or purification, is described in Sumitani et al. (2000) "New type of starch-binding domain: the direct repeat motif in the C-terminal region of *Bacillus* sp. 195 α-amylase contributes to starch binding and raw starch degrading," *Biochem. J.* 350: 477-484, and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 min. and 4° C.) and re-dissolved in 20 mM Tris/HCl buffer (pH 7.0) containing κ mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM CaCl2, and eluted at a linear flow rate of 7 mL/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, PA; Cat. No. 19812) was equilibrated with 20 mM Tris/HCl buffer (pH 7.0) containing 5 mM CaCl2 and 1.5 M (NH4)2SO4. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See, e.g., Sumitani et al. (2000) *Biochem. J.* 350: 477-484, for general discussion of the method and variations thereon.

For production scale recovery, variant α-amylase polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

4. Compositions and Uses of Variant Amylases

Variants amylases are useful for a variety of industrial applications. For example, variant amylases are useful in a starch conversion process, particularly in a saccharification process of a starch that has undergone liquefaction. The desired end-product may be any product that may be produced by the enzymatic conversion of the starch substrate. For example, the desired product may be a syrup rich in glucose and maltose, which can be used in other processes, such as the preparation of HFCS, or which can be converted into a number of other useful products, such as ascorbic acid intermediates (e.g., gluconate; 2-keto-L-gulonic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or drinking (i.e., potable alcohol). One skilled in the art is aware of various fermentation conditions that may be used in the production of these end-products. Variant amylases are also useful in compositions and methods of food preparation. These various uses of variant amylases are described in more detail below.

4.1. Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may also be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling or grinding. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. About 90% of the corn oil is in the germ. In dry milling or grinding, whole kernels are ground into a fine powder and often processed without fractionating the grain into its component parts. In some cases, oils and/or fiber from the kernels are recovered. Dry ground grain thus will comprise significant amounts of non-starch carbohydrate compounds, in addition to starch. Dry grinding of the starch substrate can be used for production of ethanol and other biochemicals. The starch to be processed may be a highly refined starch quality, for example, at least 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-amylase may be added to the slurry, with a metering pump, for example. The α-amylase typically used for this application is a thermally stable, bacterial α-amylase, such as a *Geobacillus stearothermophilus* α-amylase. The α-amylase is usually supplied, for example, at about 1500 units per kg dry matter of starch. To optimize α-amylase stability and activity, the pH of the slurry typically is adjusted to about pH 4.5-6.5 and about 1 mM of calcium (about 40 ppm free calcium ions) can also be added, depending upon the properties of the amylase used. Bacterial α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylase may be pumped continuously through a jet cooker, which is steam heated to 105° C. Gelatinization occurs rapidly under these conditions, and the enzymatic activity, combined with the significant shear forces, begins the hydrolysis of the starch substrate. The residence time in the jet cooker is brief. The partly gelatinized starch may be passed into a series of holding tubes maintained at 105-110° C. and held for 5-8 min. to complete the gelatinization process ("primary liquefaction"). Hydrolysis to the required DE is completed in holding tanks at 85-95° C. or higher temperatures for about 1 to 2 hours ("secondary liquefaction"). These tanks may contain baffles to discourage back mixing. As used herein, the term "minutes of secondary liquefaction" refers to the time that has elapsed from the start of secondary liquefaction to the time that the Dextrose Equivalent (DE) is measured. The slurry is then allowed to cool to room temperature. This cooling step can be 30 minutes to 180 minutes, e.g., 90 minutes to 120 minutes. The liquefied starch typically is in the form of a slurry having a dry solids content (w/w) of about 10-50%; about 10-45%; about 15-40%; about 20-40%; about 25-40%; or about 25-35%.

Liquefaction with variant amylases advantageously can be conducted at low pH, eliminating the requirement to adjust the pH to about pH 5.5-6.5. Variants amylases can be used for liquefaction at a pH range of 2 to 7, e.g., pH 3.0-7.5, pH 4.0-6.0, or pH 4.5-5.8. Variant amylases can maintain liquefying activity at a temperature range of about 85° C.-95° C., e.g., 85° C., 90° C., or 95° C. For example, liquefaction can be conducted with 800 µg an amylase in a solution of 25% DS corn starch for 10 min at pH 5.8 and 85° C., or pH 4.5 and 95° C., for example. Liquefying activity can be assayed using any of a number of known viscosity assays in the art.

In particular embodiments using the present amylase variants, starch liquefaction is performed at a temperature range of 90-115° C., for the purpose of producing high-purity glucose syrups, HFCS, maltodextrins, etc.

4.3. Saccharification

The liquefied starch can be saccharified into a syrup rich in lower DP (e.g., DP1+DP2) saccharides, using variant amylases, optionally in the presence of another enzyme(s). The exact composition of the products of saccharification depends on the combination of enzymes used, as well as the type of granular starch processed. Advantageously, the syrup obtainable using the provided variant amylases may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%. The present amylases also produce a relatively high yield of glucose, e.g., DP1>20%, in the syrup product.

Whereas liquefaction is generally run as a continuous process, saccharification is often conducted as a batch process. Saccharification typically is most effective at temperatures of about 60-65° C. and a pH of about 4.0-4.5, e.g., pH 4.3, necessitating cooling and adjusting the pH of the liquefied starch. The temperature and pH range can vary depending upon the properties of the enzymes. Saccharification may be performed, for example, at a temperature between about 40° C., about 50° C., or about 55° C. to about 60° C. or about 65° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min., for example. Further incubation will result in a lower DE, eventually to about 90 DE, as accumulated glucose re-polymerizes to isomaltose and/or other reversion products via an enzymatic reversion reaction and/or with the approach of thermodynamic equilibrium.

When using an amylase, saccharification optimally is conducted at a temperature range of about 30° C. to about 75° C., e.g., 45° C.-75° C. or 47° C.-74° C. The saccharifying may be conducted over a pH range of about pH 3 to about pH 7, e.g., pH 3.0-pH 7.5, pH 3.5-pH 5.5, pH 3.5, pH 3.8, or pH 4.5.

An α-amylase may be added to the slurry in the form of a composition. An α-amylase can be added to a slurry of a granular starch substrate in an amount of about 0.6-10 ppm ds, e.g., 2 ppm ds. An α-amylase can be added as a whole broth, clarified, enriched, partially purified, or purified enzyme. The specific activity of the amylase may be about 300 U/mg of enzyme, for example, measured with the PAHBAH assay. The α-amylase also can be added as a whole broth product.

An α-amylase may be added to the slurry as an isolated enzyme solution. For example, an α-amylase can be added in the form of a cultured cell material produced by host cells expressing an amylase. An α-amylase may also be secreted by a host cell into the reaction medium during the fermentation or SSF process, such that the enzyme is provided continuously into the reaction. The host cell producing and secreting amylase may also express an additional enzyme, such as a glucoamylase. For example, U.S. Pat. No. 5,422,267 discloses the use of a glucoamylase in yeast for production of alcoholic beverages. For example, a host cell, e.g., Trichoderma reesei or Aspergillus niger, may be engineered to co-express an α-amylase and a glucoamylase, e.g., HgGA, TrGA, or a TrGA variant, during saccharification. The host cell can be genetically modified so as not to express its endogenous glucoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanase, an isoamylase, and/or an isopullulanase. See, e.g., WO 2011/153516 A2.

4.4. Isomerization

The soluble starch hydrolysate produced by treatment with amylase can be converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5 (depending on the isomerase), and $Ca^{2+}$ is removed by ion exchange. Suitable isomerases include SWEETZYME®, IT (Novozymes A/S); G-ZYME® IMGI, and G-ZYME® G993, KETOMAX®, G-ZYME® G993, G-ZYME® G993 liquid, and GENSWEET® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 30° C. to 35° C. for alcohol-producing yeast. The temperature and pH of the fermentation will depend upon the fermenting organism. EOF products include metabolites, such as citric acid, lactic acid, succinic acid, monosodium glutamate, gluconic acid, sodium gluconate, calcium gluconate, potassium gluconate, itaconic acid and other carboxylic acids, glucono deltalactone, sodium erythorbate, lysine and other amino acids, omega 3 fatty acid, butanol, isoprene, 1,3-propanediol and other biomaterials.

Ethanologenic microorganisms include yeast, such as *Saccharomyces cerevisiae* and bacteria, e.g., *Zymomonas moblis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) Sheng Wu Gong Cheng Xue Bao 27(7): 1049-56. Commercial sources of yeast include ETHANOL RED® (LeSaffre); Thermosacc® (Lallemand); RED STAR® (Red Star); FERMIOL® (DSM Specialties); and SUPERSTART® (Alltech). Microorganisms that produce other metabolites, such as citric acid and lactic acid, by fermentation are also known in the art. See, e.g., Papagianni (2007) "Advances in citric acid fermentation by *Aspergillus niger*: biochemical aspects, membrane transport and modeling," Biotechnol. Adv. 25(3): 244-63; John et al. (2009) "Direct lactic acid fermentation: focus on simultaneous saccharification and lactic acid production," Biotechnol. Adv. 27(2): 145-52.

The saccharification and fermentation processes may be carried out as an SSF process. Fermentation may comprise subsequent enrichment, purification, and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells that express and secrete amylase continuously throughout SSF. The fungal cells expressing amylase also can be the fermenting microorganism, e.g., an ethanologenic microorganism. Ethanol production thus can be carried out using a fungal cell that expresses sufficient amylase so that less or no enzyme has to be added exogenously. The fungal host cell can be from an appropriately engineered fungal strain. Fungal host cells that express and secrete other enzymes, in addition to amylase, also can be used. Such cells may express glucoamylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzyme.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising Variants Amylases

Variant amylases may be combined with a glucoamylase (EC 3.2.1.3), e.g., a *Trichoderma* glucoamylase or variant thereof. An exemplary glucoamylase is *Trichoderma reesei* glucoamylase (TrGA) and variants thereof that possess superior specific activity and thermal stability. See U.S. Published Applications Nos. 2006/0094080, 2007/0004018, and 2007/0015266 (Danisco US Inc.). Suitable variants of TrGA include those with glucoamylase activity and at least 80%, at least 90%, or at least 95% sequence identity to wild-type TrGA. Variant amylases advantageously increase the yield of glucose produced in a saccharification process catalyzed by TrGA.

Alternatively, the glucoamylase may be another glucoamylase derived from plants (including algae), fungi, or bacteria. For example, the glucoamylases may be *Aspergillus niger* G1 or G2 glucoamylase or its variants (e.g., Boel et al. (1984) *EMBO J.* 3: 1097-1102; WO 92/00381; WO 00/04136 (Novo Nordisk A/S)); and *A. awamori* glucoamylase (e.g., WO 84/02921 (Cetus Corp.)). Other contemplated *Aspergillus* glucoamylase include variants with enhanced thermal stability, e.g., G137A and G139A (Chen et al. (1996) *Prot. Eng.* 9: 499-505); D257E and D293E/Q (Chen et al. (1995) *Prot. Eng.* 8: 575-582); N182 (Chen et al. (1994) *Biochem. J.* 301: 275-281); A246C (Fierobe et al. (1996) *Biochemistry,* 35: 8698-8704); and variants with Pro residues in positions A435 and S436 (Li et al. (1997) *Protein Eng.* 10: 1199-1204). Other contemplated glucoamylases include *Talaromyces* glucoamylases, in particular derived from *T. emersonii* (e.g., WO 99/28448 (Novo Nordisk A/S), *T. leycettanus* (e.g., U.S. Pat. No. RE 32,153 (CPC International, Inc.)), *T. duponti*, or *T. thermophilus* (e.g., U.S. Pat. No. 4,587,215). Contemplated bacterial glucoamylases include glucoamylases from the genus *Clostridium*, in particular *C. thermoamylolyticum* (e.g., EP 135,138 (CPC International, Inc.) and *C. thermohydrosulfuricum* (e.g., WO 86/01831 (Michigan Biotechnology Institute)). Suitable glucoamylases include the glucoamylases derived from *Aspergillus oryzae*, such as a glucoamylase shown in SEQ ID NO: 2 in WO 00/04136 (Novo Nordisk A/S). Also suitable are commercial glucoamylases, such as AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR (*A. niger* glucoamylase with a low protease content). Still other suitable glucoamylases include *Aspergillus fumigatus* glucoamylase, *Talaromyces* glucoamylase, *Thielavia* glucoamylase, *Trametes* glucoamylase, *Thermomyces* glucoamylase, *Athelia* glucoamylase, *Humicola* glucoamylase (e.g., HgGA), *Penicillium* glucoamylase, *Artomyces* glucoamylase, *Gloeophyllum* glucoamylase, *Pycnoporus* glucoamylase, or *Steccherinum* glucoamylase. Glucoamylases typically are added in an amount of about 0.1-2 glucoamylase units (GAU)/g ds, e.g., about 0.16 GAU/g ds, 0.23 GAU/g ds, or 0.33 GAU/g ds.

Other suitable enzymes that can be used with amylase include a phytase, protease, pullulanase, β-amylase, isoamylase, a different α-amylase, alpha-glucosidase, cellulase, xylanase, other hemicellulases, beta-glucosidase, transferase, pectinase, lipase, cutinase, esterase, redox enzymes, or a combination thereof. For example, a debranching enzyme, such as an isoamylase (EC 3.2.1.68), may be added in effective amounts well known to the person skilled in the art. A pullulanase (EC 3.2.1.41), e.g., PROMOZYME®, is also suitable. Pullulanase typically is added at 100 U/kg ds. Further suitable enzymes include proteases, such as fungal and bacterial proteases. Fungal proteases include those obtained from *Aspergillus*, such as *A. niger, A. awamori, A. oryzae; Mucor* (e.g., *M. miehei*); *Rhizopus*; and *Trichoderma*.

β-Amylases (EC 3.2.1.2) are exo-acting maltogenic amylases, which catalyze the hydrolysis of 1,4-α-glucosidic linkages in amylopectin and related glucose polymers, thereby releasing maltose. β-Amylases have been isolated from various plants and microorganisms. See Fogarty et al. (1979) in Progress in Industrial Microbiology, Vol. 15, pp. 112-115. These β-Amylases have optimum temperatures in the range from 40° C. to 65° C. and optimum pH in the range from about 4.5 to about 7.0. Contemplated β-amylases include, but are not limited to, β-amylases from barley SPEZYME® BBA 1500, SPEZYME® DBA, OPTIMALT™ ME, OPTIMALT™ BBA (Danisco US Inc.); and NOVOZYM™ WBA (Novozymes A/S).

Compositions comprising the present amylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc, for example, endogenous plant (including algal) enzymes, residual enzymes from a prior processing step, and the like.

5. Compositions and Methods for Baking and Food Preparation

The present invention also relates to a "food composition," including but not limited to a food product, animal feed and/or food/feed additives, comprising an amylase, and methods for preparing such a food composition comprising mixing variant amylase with one or more food ingredients, or uses thereof.

Furthermore, the present invention relates to the use of an amylase in the preparation of a food composition, wherein the food composition is baked subsequent to the addition of the polypeptide of the invention. As used herein the term "baking composition" means any composition and/or additive prepared in the process of providing a baked food product, including but not limited to bakers flour, a dough, a baking additive and/or a baked product. The food composition or additive may be liquid or solid.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, an amylase, by itself or in combination with another α-amylase(s), may be added to the flour to augment the level of endogenous α-amylase activity in flour.

An amylase can further be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with an amylase include an endo-amylase, e.g., a bacterial endo-amylase from *Bacillus*. The additional amylase can be another maltogenic α-amylase (EC 3.2.1.133), e.g., from *Bacillus*. NOVAMYL® is an exemplary maltogenic α-amylase from *B. stearothermophilus* strain NCIB 11837 and is described in Christophersen et al. (1997) Starch 50: 39-45. Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soy bean, or from microbial sources, such as *Bacillus*.

The baking composition comprising an amylase further can comprise a phospholipase or enzyme with phospholipase activity. An enzyme with phospholipase activity has an activity that can be measured in Lipase Units (LU). The phospholipase may have A1 or A2 activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, for example The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 LU/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

The dough product may be any processed dough product, including fried, deep fried, roasted, baked, steamed and boiled doughs, such as steamed bread and rice cakes. In one embodiment, the food product is a bakery product. Typical bakery (baked) products include bread—such as loaves, rolls, buns, bagels, pizza bases etc. pastry, pretzels, tortillas, cakes, cookies, biscuits, crackers etc.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, an amadoriase, a metalloproteinase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*. Xylanases include PENTOPAN® and NOVOZYM 384®, for example, which are commercially available xylanase preparations produced from *Trichoderma reesei*. The amyloglucosidase may be an *A. niger* amyloglucosidase (such as AMG®). Other useful amylase products include GRINDAMYL® A 1000 or A 5000 (Grindsted Products, Denmark) and AMYLASE H™ or AMYLASE P™ (DSM). The glucose oxidase may be a fungal glucose oxidase, in particular an *Aspergillus niger* glucose oxidase (such as GLUZYME®). An exemplary protease is NEUTRASE®.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

An amylase may be used in a pre-mix, comprising flour together with an anti-staling amylase, a phospholipase, and/or a phospholipid. The pre-mix may contain other dough-improving and/or bread-improving additives, e.g., any of the additives, including enzymes, mentioned above. An amylase can be a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying an amylase onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Enveloped particles, i.e., α-amylase particles, can comprise an amylase. To prepare enveloped α-amylase particles, the enzyme is contacted with a food grade lipid in sufficient quantity to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated α-amylase particles, where substantially all of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results can generally be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

In a further aspect of the invention, the food composition is an oil, meat, lard, composition comprising an amylase. In this context the term "[oil/meat/lard] composition" means any composition, based on, made from and/or containing oil, meat or lard, respectively. Another aspect the invention relates to a method of preparing an oil or meat or lard composition and/or additive comprising an amylase, comprising mixing the polypeptide of the invention with a oil/meat/lard composition and/or additive ingredients.

In a further aspect of the invention, the food composition is an animal feed composition, animal feed additive and/or pet food comprising an amylase and variants thereof. The present invention further relates to a method for preparing such an animal feed composition, animal feed additive composition and/or pet food comprising mixing an amylase and variants thereof with one or more animal feed ingredients and/or animal feed additive ingredients and/or pet food ingredients. Furthermore, the present invention relates to the use of an amylase in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to dogs, cats, gerbils, hamsters, chinchillas, fancy rats, guinea pigs; avian pets, such as *canaries*, parakeets, and parrots; reptile pets, such as turtles, lizards and snakes; and aquatic pets, such as tropical fish and frogs.

The terms "animal feed composition," "feedstuff" and "fodder" are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins

6. Textile Desizing Compositions and Use

Also contemplated are compositions and methods of treating fabrics (e.g., to desize a textile) using an amylase. Fabric-treating methods are well known in the art (see, e.g., U.S. Pat. No. 6,077,316). For example, the feel and appearance of a fabric can be improved by a method comprising contacting the fabric with an amylase in a solution. The fabric can be treated with the solution under pressure.

An amylase can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An amylase can be applied during or after the weaving to remove these sizing starch or starch derivatives. After weaving, an amylase can be used to remove the size coating before further processing the fabric to ensure a homogeneous and wash-proof result.

An amylase can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An amylase can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an amylase as a component. An amylase polypeptide can be used as a component in detergent compositions for, e.g., hand washing, laundry washing, dishwashing, and other hard-surface cleaning. Such compositions include heavy duty liquid (HDL), heavy duty dry (HDD), and hand (manual) laundry detergent compositions, including unit dose format laundry detergent compositions, and automatic dishwashing (ADW) and hand (manual) dishwashing compositions, including unit dose format dishwashing compositions.

7.1. Overview

Preferably, an amylase is incorporated into detergents at or near a concentration conventionally used for amylase in detergents. For example, an amylase polypeptide may be added in amount corresponding to 0.00001-1 mg (calculated as pure enzyme protein) of amylase per liter of wash/dishwash liquor. Exemplary formulations are provided herein, as exemplified by the following:

An amylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, bars, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a H2O2 source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibitors, optical brighteners, or perfumes.

The pH (measured in aqueous solution at use concentration) is usually neutral or alkaline, e.g., pH about 7.0 to about 11.0.

Particular forms of detergent compositions for inclusion of the present α-amylase are described, below. Many of these composition can be provided in unit dose format for ease of use. Unit dose formulations and packaging are described in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a C8-C18 alkyl ethoxylated alcohol and/or C6-C12 alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and copolymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated C12-C24 fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally include silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted C8-C18 alkyl ethoxylates, and/or C6-C12 alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photo-bleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroamines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

7.4. Automatic Dishwashing (ADW) Detergent Composition

Exemplary ADW detergent composition includes non-ionic surfactants, including ethoxylated non-ionic surfactants, alcohol alkoxylated surfactants, epoxy-capped poly (oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninedi-acetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., C12-18 alcohol, 1-2 ethylene oxide (EO)) or alkyl sulfate (e.g., C16-18) about 1% to about 4%; alcohol ethoxylate (e.g., C14-15 alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7$/$C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., C12-18 alcohol, 1-2 EO) or alkyl sulfate (e.g., C16-18) about 1% to about 3%; alcohol ethoxylate (e.g., C14-15 alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7$/$C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., C12-15 alcohol, 7 EO) about 7% to about 14%; Soap as fatty acid (e.g., C16-22 fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., C12-15 alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., C12-15 alcohol, 7 EO or C12-15 alcohol, 5 EO) about 12% to about 18%; soap as fatty acid (e.g., oleic acid) about 3% to about 13%; alkenylsuccinic acid (C12-14) 0% to about 13%; aminoethanol about 8% to about 18%; citric acid about 2% to about 8%; phosphonate 0% to about 3%; polymers (e.g., PVP, PEG) 0% to about 3%; borate (e.g., B4O7) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., C12-15 alcohol, 7 EO, or C12-15 alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., B4O7) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., Na2CO3) about 5% to about 10%; Soluble silicate (e.g., $Na_2O$, 2SiO2) about 1% to about 4%; zeolite (e.g., NaAlSiO4) about 20% to about 40%; Sodium sulfate (e.g., Na2SO4) about 2% to about 8%; sodium perborate (e.g., NaBO3H2O) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., Na2CO3) about 4% to about 10%; soluble silicate (Na2O, 2SiO2) about 1% to about 4%; zeolite (e.g., NaAlSiO4) about 30% to about 50%; sodium sulfate (e.g., Na2SO4) about 3% to about 11%; sodium citrate (e.g., C6H5Na3O7) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., Na2CO3) about 14% to about 22%; zeolite (e.g., NaAlSiO4) about 18% to about 32%; sodium sulfate (e.g., Na2SO4) about 5% to about 20%; sodium citrate (e.g., C6H5Na3O7) about 3% to about 8%; sodium perborate (e.g., NaBO3H2O) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., C12-15 alcohol, 2-3 EO) about 8% to about 15%; alcohol ethoxylate (e.g., C12-15 alcohol, 7 EO, or C12-15 alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., B4O7) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., C12-15 alcohol, 7 EO, or C12-15 alcohol, 5 EO) 6-12%; aminoethanol about 2% to about 6%; citric acid about 8% to about 14%; borate (e.g., B4O7) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., Na2CO3) about 8% to about 25%; soluble silicates (e.g., Na2O, 2SiO2) about 5% to about 15%; sodium sulfate (e.g., Na2SO4) 0% to about 5%; zeolite (NaAlSiO4) about 15% to about 28%; sodium perborate (e.g., NaBO3.4H2O) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by (C12-C18) alkyl sulfate.

14) A detergent composition formulated as a granulate having a bulk density of at least 600 g/L comprising (C12-C18) alkyl sulfate about 9% to about 15%; alcohol ethoxylate about 3% to about 6%; polyhydroxy alkyl fatty acid amide about 1% to about 5%; zeolite (e.g., NaAlSiO4) about 10% to about 20%; layered disilicate (e.g., SK56 from Hoechst) about 10% to about 20%; sodium carbonate (e.g., Na2CO3) about 3% to about 12%; soluble silicate (e.g., Na2O, 2SiO2) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising (C12-C18) alkyl sulfate about 4% to about 8%; alcohol ethoxylate about 11% to about 15%; soap about 1% to about 4%; zeolite MAP or zeolite A about 35% to about 45%; sodium carbonate (as Na2CO3) about 2% to about 8%; soluble silicate (e.g., Na2O, 2SiO2) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," Nature 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases: Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Additional examples include those mutant proteases described in U.S. Pat. Nos. RE 34,606, 5,955,340, 5,700,676, 6,312,936, and 6,482,628, all of which are incorporated herein by reference. Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: Alcalase®, Savinase®, Primase™, Duralase™, Esperase®, BLAZE™ POLARZYME®, OVOZYME®, KANNASE®, LIQUANASE®, NEUTRASE®, RELASE®, and ESPERASE® (Novo Nordisk A/S and Novozymes A/S), Maxatase®, Maxacal™ Maxapem™, Properase®, Purafect®, Purafect OxP™, Purafect Prime™ FNA™ FN2TM FN3™, OPTICLEAN®, OPTIMASE®, PURAMAX™, EXCELLASE™, and PURAFAST™ (Danisco US Inc./DuPont Industrial Biosciences, Palo Alto, California, USA), BLAP™ and BLAP™ variants (Henkel Kommanditgesellschaft auf Aktien, Duesseldorf, Germany), and KAP (*B. alkalophilus* subtilisin; Kao Corp., Tokyo, Japan). Another exemplary proteases NprE from *Bacillus amyloliquifaciens* and ASP from *Cellulomonas* sp. strain 69B4 (Danisco US Inc./DuPont Industrial Biosciences, Palo Alto, California, USA). Various proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500, 364, 5,855,625, US RE 34,606, 5,955,340, 5,700,676, 6,312, 936, and 6,482,628, and various other patents. In some further embodiments, metalloproteases find use in the present invention, including but not limited to the neutral metalloprotease described in WO 07/044993. Suitable proteases include naturally occurring proteases or engineered variants specifically selected or engineered to work at relatively low temperatures.

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens*, *Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. Biochemica et Biophysica Acta, 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase Ultra™ (Novo Nordisk A/S and Novozymes A/S).

Polyesterases: Suitable polyesterases can be included in the composition, such as those described in, for example, WO 01/34899, WO 01/14629, and U.S. Pat. No. 6,933,140.

Amylases: The present compositions can be combined with other amylases, including other α-amylases. Such a combination is particularly desirable when different α-amylases demonstrate different performance characteristics and the combination of a plurality of different α-amylases results in a composition that provides the benefits of the different α-amylases. Other amylases include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, PURASTAR®, and PREFERENZ™ (from DuPont Industrial Biosciences).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S and Novozymes A/S); CLAZINASE® and PURADAX HA® (DuPont Industrial Biosciences); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Numerous exemplary detergent formulations to which the present amylases can be added (or is in some cases are identified as a component of) are described in WO2013063460. These include commercially available unit dose detergent formulations/packages such as PUREX® UltraPacks (Henkel), FINISH® Quantum (Reckitt Benckiser), CLOROX™ 2 Packs (Clorox), OxiClean Max Force Power Paks (Church & Dwight), TIDE® Stain Release, CASCADE® ActionPacs, and TIDE® Pods™ (Procter & Gamble), PS.

7.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

8. Brewing Compositions

The present variant amylase may be a component of a brewing composition used in a process of brewing, i.e., making a fermented malt beverage. Non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces of beer. an amylase, in combination with a glucoamylase and optionally a pullulanase and/or isoamylase, assist in converting the starch into dextrins and fermentable sugars, lowering the residual non-fermentable carbohydrates in the final beer.

The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has the greatest effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops act as protein precipitants, establish preservative agents and aid in foam formation and stabilization.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. an amylase, by itself or in combination with another α-amylase(s), accordingly may be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer. Typically, milled or crushed malt is mixed with water and held for a period of time under controlled temperatures to permit the enzymes present in the malt to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilizes the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast flocculates and is removed. Finally, the beer is cooled and stored for a period of time, during which the beer clarifies and its flavor develops, and any material that might impair the appearance, flavor and shelf life of the beer settles out. The beer usually contains from about 2% to about 10% v/v alcohol, although beer with a higher alcohol content, e.g., 18% v/v, may be obtained. Prior to packaging, the beer is carbonated and, optionally, filtered and pasteurized.

The brewing composition comprising an amylase, in combination with a glucoamylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

A fermented beverage, such as a beer, can be produced by one of the methods above. The fermented beverage can be a beer, such as full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

9. Reduction of Iodine-Positive Starch

Variant amylases may reduce the iodine-positive starch (IPS), when used in a method of liquefaction and/or saccharification. One source of IPS is from amylose that escapes hydrolysis and/or from retrograded starch polymer. Starch retrogradation occurs spontaneously in a starch paste, or gel on ageing, because of the tendency of starch molecules to bind to one another followed by an increase in crystallinity. Solutions of low concentration become increasingly cloudy due to the progressive association of starch molecules into larger articles. Spontaneous precipitation takes place and the precipitated starch appears to be reverting to its original condition of cold-water insolubility. Pastes of higher concentration on cooling set to a gel, which on ageing becomes steadily firmer due to the increasing association of the starch molecules. This arises because of the strong tendency for hydrogen bond formation between hydroxy groups on adjacent starch molecules. See J. A. Radley, ed., Starch and its Derivatives 194-201 (Chapman and Hall, London (1968)).

The presence of IPS in saccharide liquor negatively affects final product quality and represents a major issue with downstream processing. IPS plugs or slows filtration system, and fouls the carbon columns used for purification. When IPS reaches sufficiently high levels, it may leak through the carbon columns and decrease production efficiency. Additionally, it may results in hazy final product upon storage, which is unacceptable for final product quality. The amount of IPS can be reduced by isolating the saccharification tank and blending the contents back. IPS nevertheless will accumulate in carbon columns and filter systems, among other things. The use of variant amylases is expected to improve overall process performance by reducing the amount of IPS.

All references cited herein are herein incorporated by reference in their entirety for all purposes. In order to further illustrate the compositions and methods, and advantages thereof, the following specific examples are given with the understanding that they are illustrative rather than limiting.

EXAMPLES

Example 1

Assays

Various assays used herein are set forth, below, for ease in reading. Any deviations from the protocols in later Examples are indicated in the relevant sections. In these experiments, a spectrophotometer was used to measure the absorbance of the products formed after the completion of the reactions.

A. Protein Purification

*Bacillus* strains expressing amylase variants were grown in 2.5 L flasks in cultivation medium (enriched semi-defined media based on MOPs buffer, with urea as the major nitrogen source, glucose as the main carbon source, and supplemented with 1% soytone for robust cell growth) for 60-72 hours at 37° C. or in 14 L tanks using a fed batch fermentation process with a medium of corn steep and soy flour supplemented with mineral salts and glucose as carbon source for 100 hours at 36° C. Following incubation, the cells were separated from the fermentation medium by centrifugation and the supernatants were concentrated by ultra-filtration. Ammonium sulphate was added to the concentrate to a final concentration of 0.5M. The proteins were purified using hydrophobic interaction chromatography using a phenyl sepharose column on the AKTA Explorer FPLC system (GE Healthcare). The column was equilibrated with 50 mM HEPES, pH 8, with 2 mM $CaCl_2$ and 0.5 M ammonium sulfate, and the proteins were eluted with 50 mM HEPES, pH 8, with 2 mM $CaCl_2$ and 50% propylene glycol. After each HPLC run, liquid fractions associated with the peak of interest were pooled, and absorbance measurements of the pooled fractions were taken to estimate initial concentrations. Protein concentration of concentrated samples was determined by averaging the result from three different measurements: absorbance measurements at 280 nm, SDS-PAGE densitometry of acid-treated samples compared to a known standard, and by running the proteins on an HPLC system and taking absorbance measurements at 215 nm and 280 nm.

B. Ceralpha α-Amylase Activity Assay

The Ceralpha α-amylase assay was performed using the Ceralpha Kit (Megazyme, Wicklow, Ireland). The assay involves incubating culture supernatant with a substrate mixture under defined conditions, and the reaction is terminated (and color developed) by the addition of borate buffer (200 mM Boric acid/NaOH buffer, pH 10). The substrate is a mixture of the defined oligosaccharide "nonreducing-end blocked p-nitrophenyl maltoheptaoside" (BPNPG7) and excess levels of α-glucosidase (which has no action on the native substrate due to the presence of the "blocking group"). On hydrolysis of the oligosaccharide by endoacting α-amylase, the excess quantities of α-glucosidase present in the mixture give instantaneous and quantitative hydrolysis of the p-nitrophenyl maltosaccharide fragment to glucose and free p-nitrophenol. The absorbance at 405 nm was measured, which relates directly to the level of amylase in the sample analyzed.

The equipment used for this assay included a Biomek FX Robot (Beckman Coulter Brea, CA, USA); a SpectraMAX MTP Reader (type 340-Molecular Devices, Sunnyvale, CA, USA) and iEMS incubator/shaker (Thermo Scientific, Rockford, IL, USA). The reagent and solutions used were:

1) p-nitrophenyl maltoheptaoside (BPNPG7) substrate (Megazyme Ceralpha HR kit);
2) 50 mM Malate buffer, 0.005% TWEEN® 80, pH 5.6 or 50 mM MOPS, 0.005% TWEEN® 80, pH 7 (dilution buffers); and
3) 200 mM Boric acid/NaOH buffer, pH 10 (STOP buffer).

A vial containing 54.5 mg BPNPG7 substrate was dissolved in 10 mL of MilliQ water and then diluted into 30 mL of dilution buffer to make up 40 mL of the working substrate (1.36 mg/mL). The amylase samples (fermentation supernatant) were diluted 40× with dilution buffer. The assay was performed by adding 5 μL of diluted amylase solution into the wells of a MTP followed by the addition of 55 μL of diluted BPNPG7 working substrate solution. The solutions were mixed and the MTP was sealed with a plate seal and placed in an incubator/shaker (iEMS—Thermo Scientific) for 4 minutes at 25° C. The reaction was terminated by adding 70 μL STOP buffer and the absorbance was read at wavelength 400 nm in an MTP-Reader. A non-enzyme control was used to correct for background absorbance values.

C. Thermostability Assay

The thermostability of CspAmy2-v1 and variants was measured by determining the amylase activity using the Ceralpha α-amylase assay. The equipment used for this assay included a Biomek FX Robot (Beckman Coulter); a SpectraMAX MTP Reader (type 340-Molecular Devices), a Tetrad2DNA Engine PCR machine (Biorad), and iEMS incubator/shaker (Thermo Scientific). The reagent solutions used were (* not in all assays):

1) Heat stress buffers
   a) 50 mM KOAc pH 4.5 (5 ppm $CaCl_2$, 50 ppm NaCl)*,
   b) 50 mM KOAc pH 5.0 (10 ppm $CaCl_2$, 10 mM NaCl)
   c) 50 mM KOAc pH 5.7 (5 ppm $CaCl_2$, 50 ppm NaCl),
   d) 50 mM KOAc pH 5.7 (no salt condition)*,
2) p-nitrophenyl maltoheptaoside (BPNPG7) substrate (Megazyme Ceralpha HR kit):
3) 50 mM Malate buffer, 0.005% TWEEN® 80, pH 5.6 (dilution buffer); and
4) 200 mM Boric acid/NaOH, pH 10 (STOP buffer).
5) Amylase culture supernatant: 1:10 master dilution enzyme plates were diluted 1:10 in each of the four heat stress buffers in a PCR plate 5 μL of the diluted enzyme samples were added to a 96-well PCR plate containing 55 μL of diluted BPNPG7 working substrate solution and the initial amylase activity of the samples was determined using the Ceralpha α-amylase assay as described in Section C. The samples were subjected to heat stress for 3-6 minutes in a PCR thermocycler as follows: Buffers (a) 50° C., (b) 59°-60° C., (c) 65°-70° C., and (d) 65° C. The heat stressed samples were cooled immediately to room temperature and 5 μL aliquots were assayed for amylase activity using the Ceralpha α-amylase assay as described in Section C. For each variant, the ratio of the initial and residual amylase activities was used to calculate the thermostability as follows: Thermostability= $[t_{residual}$ value$]/[t_{initial}$ value], so the heat stability activity ratio was calculated based on enzyme activity after heat incubation divided by enzyme activity before heat incubation. For each sample (variants) the performance index (PI) is calculated. The performance index for thermostability stability is determined by comparing the thermostability of the variant enzyme with that of a similarly treated reference enzyme.

D. Starch Hydrolysis Assays (Corn Flour and Corn Starch Application Assays)

Starch hydrolysis of corn flour and corn starch were used to measure specific activity of CspAmy2-v1 and variants. Activity was measured as reducing ends generated by the enzymatic breakdown of corn flour or corn starch. The reducing ends generated during the incubation with either substrate were quantified using a PAHBAH (p-hydroxybenzoic acid hydrazide) assay. The equipment used for the assay included a Biomek FX Robot (Beckman Coulter); a SpectraMAX MTP Reader (type 340-Molecular Devices), a Tetrad2DNA Engine PCR machine (Biorad), and iEMS incubator/shaker (Thermo Scientific), and a Bubble Paddle Reservoir.

Azure Farms Organic Corn Flour (Norco, CA) was ground to a fine powder using a consumer coffee grinder and then sifted to obtain a <250 micron fraction. The sifted corn flour was washed extensively with MilliQ water by repeated suspension and centrifugation. Cargill Farms Organic Corn Starch material was also washed extensively with MilliQ water by repeated suspension and centrifugation.

Both corn flour and corn starch washed fractions were suspended in MilliQ water containing 0.005% sodium azide as 20% (w/w) stock solutions. The stock solutions were further diluted with a 20× stock buffer solution to 10.9% w/v corn flour and corn starch solutions (final buffer concentration: 55 mM KOAc, pH 5).

55 µL of the diluted corn flour and corn starch substrates were added to PCR microtiter plates along with 5 µL of 1:10 diluted enzyme samples using a bubble paddle reservoir. The plates were sealed and placed at 83° C. for 5 minutes followed by a ramp down to 45° C. The starch hydrolysis reaction was terminated by addition of 70 µL 0.1 N NaOH. The plates were sealed and centrifuged for 3 minutes at 1610 RCF. The starch hydrolysis reaction products from both reactions were analyzed by the PAHBAH assay as described below.

PAHBAH Assay:

Aliquots of 80 µL of 0.5 N NaOH were added to all wells of an empty PCR plate (a "PAHBAH reaction plate"), followed by 20 µL of PAHBAH reagent (5% w/v p-hydroxybenzoic acid hydrazide (Sigma #H9882, St. Louis, MO), dissolved in 0.5 N HCl). The solutions were mixed by pipetting up and down. 20 µL of the starch hydrolysis reaction supernatants were added to each well of the PAHBAH reaction plate. The plates were sealed and placed in a thermocycler, programmed for 2 minutes at 95° C. to develop color, and then cooled to 20° C. Samples of 80 µL of the developed PAHBAH reaction mixtures were transferred to a fresh plate, and absorbance was measured at 450 nm in a spectrophotometer.

E. Cleaning Performance Assays

1. Small Scale—CS-28 Rice Starch Microswatch Assay

The principle of this amylase assay is the liberation of an orange dye due to the hydrolysis of rice starch incorporated in a cotton microswatch. The absorbance at 488 nm of the wash liquid is measured and this relates to the level of amylase activity in the sample analyzed at the desired conditions (pH, temperature, and buffer).

The equipment used for this assay included a Biomek FX Robot (Beckman Coulter), a SpectraMAX MTP Reader (type 340-Molecular Devices) and iEMS incubator/shaker (Thermo Scientific). The reagent and solutions used were:
1) CS-28 Microswatches (rice starch, colored);
2) 10 mM HEPES, 2 mM $CaCl_2$, 0.005% TWEEN 80 buffer, pH 8.0, conductivity 1 mS/cm;
3) 25 mM CAPS, 2 mM $CaCl_2$, 0.005% TWEEN 80 buffer, pH 10.0; conductivity 5 mS/cm (adjusted with 5M NaCl); and
4) 10 mM NaCl, 0.1 mM $CaCl_2$, 0.005% TWEEN 80.
5) 50 mM MOPS pH7.15, 0.1 mM $CaCl_2$ CS-28 microswatches of 5.5 mm circular diameter were provided by the Center for Testmaterials (CFT, Vlaardingen, The Netherlands). Two microswatches were placed in each well of a 96-well Corning 9017 flat bottomed polystyrene MTP. The culture supernatants were diluted eight fold in 50 mM MOPS pH7.15, 0.1 mM $CaCl_2$, and subsequently in 10 mM NaCl, 0.1 mM $CaCl_2$, 0.005% TWEEN®80 solution to approximately 1 ppm, final enzyme concentration.

The incubator/shaker was set at the desired temperature, 25° C. (ambient temperature) or 50° C. 174 µL or 177 µL of either HEPES or CAPS buffer, respectively, was added to each well of microswatch containing MTP and subsequently 6 µL or 3 µL of diluted enzyme solution was added to each well resulting in a total volume of 180 µL/well. The MTP was sealed with a plate seal and placed in the iEMS incubator/shaker and incubated for 15 minutes at 1150 rpm at 25° C. for cleaning at pH 8, low conductivity (1 mS/cm), or 15 minutes at 1150 rpm at 50° C. for cleaning at pH 10, high conductivity (5 mS/cm). Following incubation under the appropriate conditions, 100 µL of solution from each well was transferred to a new MTP, and the absorbance at 488 nm was measured using a MTP-spectrophotometer. Controls containing two microswatches and buffer but no enzyme were included for subtraction of background cleaning performance Each absorbance value was corrected by subtracting the blank (obtained after incubation of microswatches in the absence of enzyme), and the resulting absorbance provided a measure of the hydrolytic activity. A performance index (PI) was calculated for each sample.

For calculation of the wash performance indices (PI), the Langmuir equation was used to fit the data based on the reference enzyme control. Using the protein concentration of the variants, the expected performance based on the curve-fit was calculated. The observed performance was divided by the calculated performance. This value was then divided by the performance of the reference enzyme.

2. Mid-Scale Cleaning Performance Method

Stain removal from swatches was tested under similar conditions as above, but at medium-scale, and with heat-inactivated commercial KIRKLAND SIGNATURE® detergent. Heat inactivation of detergents serves to destroy the activity of enzymatic components while retaining the properties of non-enzymatic components. Heat inactivation was performed by placing pre-weighed liquid detergent (in a glass bottle) in a water bath at 90° C. for 4 hours. Both unheated and heated detergents were assayed to accurately determine the percentage enzyme deactivation, using the Suc-AAPF-pNA and Ceralpha substrate assays, for measuring protease and amylase activity, respectively.

Wash treatment was conducted in 1 L in a Terg-o-tometer. Each pot was filled with deionized water and the water hardness was adjusted to 6 grains per gallon (gpg) using a 15,000 gpg 3:1 Ca:Mg water hardness stock solution. Heat inactivated Kirkland Signature® detergent (0.8 g/L) was added, and the temperature was adjusted to 16° C. The amylases to be evaluated were added to a final concentration of 0.02, 0.05, 0.1, 0.3, or 0.5 ppm. Cotton ballast was added to each pot to provide 30 g/L total fabric load. After a 13 min wash with agitation at 100 rpm, swatches were rinsed in cold tap water, and spun in a front-loading washing machine for 7 minutes at a 1000 rpm spin cycle. After washing, the swatches were machine-dried at low heat and the optical reflectance was measured as described above.

3. Full-Scale Cleaning Method

Stain removal from swatches was tested under buffered conditions at pH 8.0 with heat-inactivated commercial KIRKLAND SIGNATURE ULTRA CLEAN™ detergent.

The amount of soil on each of the test swatches was measured before and after treatment by optical reflectance using a Konica Minolta Handheld Spectrophotometer CM-600D set to a D65 (6500° K) standard illuminant. The difference in the L, a, b values was converted to total color difference (dE), as defined by the CIE-LAB color space. Cleaning of the stains was expressed as percent stain removal index (% SRI) by taking a ratio between the color difference before and after washing and comparing it to the difference of unwashed soils (before wash) to unsoiled fabric. Four swatches of each type of soil were included in two washing machines run under identical conditions. The middle area of each swatch was scanned, to yield a total of eight measurements per soil. Wash treatment was conducted in 58 L in a Maytag Century Washing Machine. The washing machine was filled with water using the 'Cold Auto Temperature' setting and the water hardness was adjusted to 6 grains per gallon (gpg) using a 15,000 gpg 3:1 Ca:Mg water hardness stock solution. Heat inactivated KIRKLAND SIGNATURE ULTRA CLEAN™ detergent (0.75 g/L) was added, and the temperature was adjusted to 16° C. An aliquot of the protease PURAFECT® Prime HA, (DuPont Industrial Biosciences) was added to a final concentration of 0.43 ppm, and the α-amylases to be evaluated were added to a final concentration of 0.043 ppm. A mixture of cotton towels, cotton T-shirts, and poly-cotton sheets was added as ballast to provide 40 g/L total fabric load. The wash conditions were as follows: 13 min wash with a 2.5 min deep-water rinse, rinse temperature of 16° C., fast agitation, and fast spin. After washing, the swatches were machine-dried at low heat and the optical reflectance was measured as described above.

F. Detergent Stability Assays

The commercial liquid detergent PERSIL BIO® (Unilever) was purchased and heat inactivated as described above. To prepare the samples, protease (PURAFECT® Prime HA) and amylases were added to each detergent sample and mixed, such that the final concentration in the wash would be 0.5 and 0.05 ppm, respectively. Samples were stored in a $CO_2$ incubator (Sanyo) at 37° C., and aliquots were taken from each reaction sample at various time points, diluted in 50 mM MOPS, pH 7.15 buffer with 1% BSA added, and alpha-amylase activity was measured using the Ceralpha substrate (Megazyme, Inc). The activity for each sample was determined using an Arena 20XT Photometric Analyzer (Thermo Scientific) using a calibrated standard. The remaining activity after incubation was reported as a percent of the total activity determined at time zero.

The stability of the reference amylase and variants thereof was determined by measuring their activity after incubation under defined conditions, in the presence of a 10% detergent mixture (commercially purchased PERSIL COLOR GEL® detergent, Henkel (Düsseldorf, Germany), purchased in 2011). The detergent was heat-inactivated before use, diluted with water, and the initial and residual amylase activities were determined using the Ceralpha α-amylase assay as described, above.

G. Thermostability

Variants were tested for thermal stability in 50 mM potassium acetate, 0.125 mM $CaCl_2$, and 2.2 mM NaCl at a preselected temperature (default is 85° C.) and desired pH. Stock solutions of each variant were prepared by diluting purified variants to a final protein concentration of 1 mg/mL in milli-Q water, then each variant was further diluted (200-fold) in each of the above buffers (final enzyme dose is 5 µg/mL). The diluted enzyme solutions were pre-heated to appropriate temperature for two minutes and then cooled on ice to disrupt any protein aggregates. 50 µL of each enzyme solution was transferred to 0.2 mL PCR strip tubes, which were heated to the appropriate temperature (based on buffer pH) and allowed to incubate over a two-hour period. The samples were then placed in an ice-water bath to end the heat-stress period.

Once all time points were collected for each buffer, residual activity was determined using the Ceralpha assay, as described in Example 1. Two independent inactivation time-course experiments were performed for each variant. Plots of residual activity vs. time were modeled with a single exponential decay equation to determine a rate constant (k) for decay. The half-life of decay was defined as ln(2)/k. These experiments were performed in duplicate for each variant.

The performance index (PI) for each variant was defined as the ratio of the variant half-life to the half-life of a reference parent molecule.

H. Peak and Final Fluidity/Viscometer Assays

A Rapid Visco Analyzer (RVA Super4, Perten Instruments, Hägersten, Sweden) was used to measure the ability of an enzyme to break the viscosity of a corn flour slurry at high temperature. Corn flour was mixed with DI water to prepare 33 g of a 25% ds slurry into RVA aluminum cans (sample cans and double skirted stirring paddles, Perten Instruments, Hägersten, Sweden). The pH of the slurry was adjusted to pH 5.0 with 1 N sulfuric acid. The Rapid Visco Analyzer program was loaded to start at 70° C. with an immediate ramp to and hold at 95° C. Upon enzyme addition, a double skirted paddle was placed on the can and immediately put into the RVA for a total run time of 10 minutes. Viscosity was continuously measured and collected by the RVA over the entire run. Enzymes were tested at 10, 30, and 50 µg. The plots show the protein dose dependence of the peak fluidity (1/cP), which is the inverse of viscosity at the peak of viscosity change and that of the final fluidity (1/cP), which is the inverse of viscosity at the end of viscosity change.

Example 2

Generation of CspAmy2 Variants

The generation of *Bacillus* strains expressing variants of CspAmy2 is described in WO 2014/164777 as are the variants in Table 2, wherein deletions at positions R178 and G179 are indicated by "del (R178, G179)" and amino acid position numbering refers to SEQ ID NO: 1:

TABLE 2

Previously described CspAmy2 variants

| Variant | Mutations |
| --- | --- |
| CspAmy2-v5 | del (R178, G179) + E187P + I203Y + G476K |
| CspAmy2-v6 | del (R178, G179) + T180D + E187P + I203Y + R458N + T459S + D460T + G476K |
| CspAmy2-C16E | del (R178, G179) + N126Y + F153W + T180H + E187P + I203Y |
| CspAmy2-C16F | del (R178, G179) + N126Y + F153W + T180D + I203Y + S241Q |
| CspAmy2-v186 | del (R178, G179) + T38N + N88H + N126Y + T129I + N134M + F153W + L171R + T180D + E187P + I203Y + G476K + G477E |

Example 3

Additional CspAmy2 Variants Based on C16E and C16F

The additional variants listed in Table 3, based CspAmy2-C16E and CspAmy2-C16F (abbreviated C16E and C16F, respectively), were constructed as described in WO 2014/164777. It will be abbreviated that all the additional variant include all the mutations of C16E or C16F. As above, amino acid position numbering refers to SEQ ID NO: 1.

TABLE 3

C16E and C16F-based variants

| Variant | Name |
|---|---|
| C16E + S360A | C16E-A |
| C16E + R375Y | C16E-Y |
| C16E + S360A + R375Y | C16E-AY |
| C16E + S360A + R375Y +T89E | C16E-AY |
| C16F + S360A | C16F-A |
| C16F + R375Y | C16F-Y |
| C16F + S360A + R375Y | C16F-AY |
| C16F + G474C | C16F-G |

The low pH stability (i.e., half-life values in seconds) of the above molecules was tested substantially as described in Example 1 at pH 4.5, 4.8, and 5.0, and compared to C16E and C16F. All enzymes were very stable at pH 5.3 at 99° C. in the 20 minute assay. Thermal inactivation was observed only at the lower pH values. At these lower pH values, variants C16E-AY and C16E-Y had the highest thermal stability. The half-life values (in seconds) of each of the variants at each pH are shown in the Table 4.

TABLE 4

Low pH stability of C16E and C16F variants

| Variant | pH | | |
|---|---|---|---|
|  | 4.50 | 4.80 | 5.00 |
| C16E | 407 | 634 | 1448 |
| C16F | 254 | 565 | 1281 |
| C16E-A | 441 | 683 | 2928 |
| C16E-Y | 488 | 1403 | 2587 |
| C16E-AY | 505 | 887 | 950 |
| C16F-A | 289 | 495 | 1153 |
| C16F-Y | 269 | 451 | 984 |
| C16F-AY | 258 | 553 | 797 |
| C16F-C | 464 | 394 | 217 |

Figure 2:
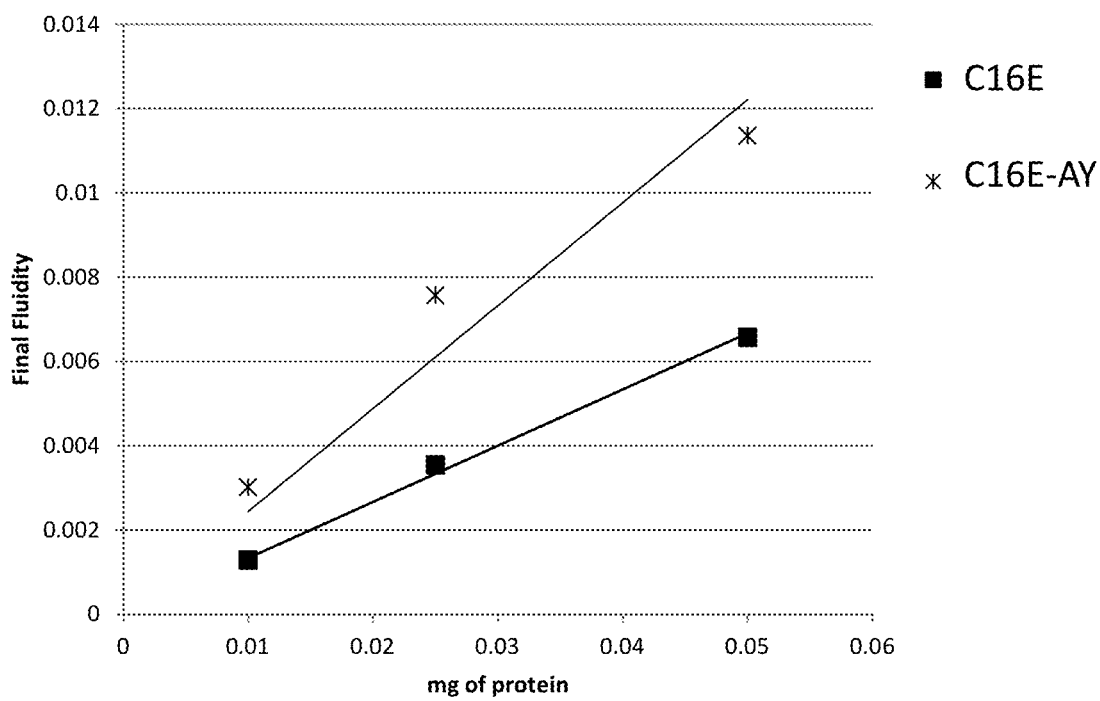
FIG. 2 is a graph showing final fluidity values per mg enzyme resulting from incubation of the starch substrate with α-amylase variants C16E and C16E-AY.

Peak and final fluidity viscosity was measured as described in Example 1. Peak fluidity values per mg enzyme resulting from incubation of the starch substrate with variants C16E and C16E-AY are shown in FIG. 1. Final fluidity values are shown in FIG. 2.

Example 4

Further Additional CspAmy2 Variants Based on C16E

Further additional variants based on C16E were constructed as described in WO 2014/164777. The names of the variants and mutations present are shown in Table 5. Note that the mutation W153F represents a reversion to the wild-type residue at position 153. Therefore, C16E-AY-W153F does not have a mutation at position 153 with respect to CspAmy2.

TABLE 5

Further C16E-based variants

| Variant | Name |
|---|---|
| C16E + S360A + R375Y + A275E | C16E-AY-A275E |
| C16E + S360A + R375Y + A275D | C16E-AY-A275D |
| C16E + S360A + R375Y + W153F | C16E-AY-W153F |
| C16E + S360A + R375Y + S92R | C16E-AY-S92R |
| C16E + S360A + R375Y + Y301A | C16E-AY-Y301A |

Figure 3:
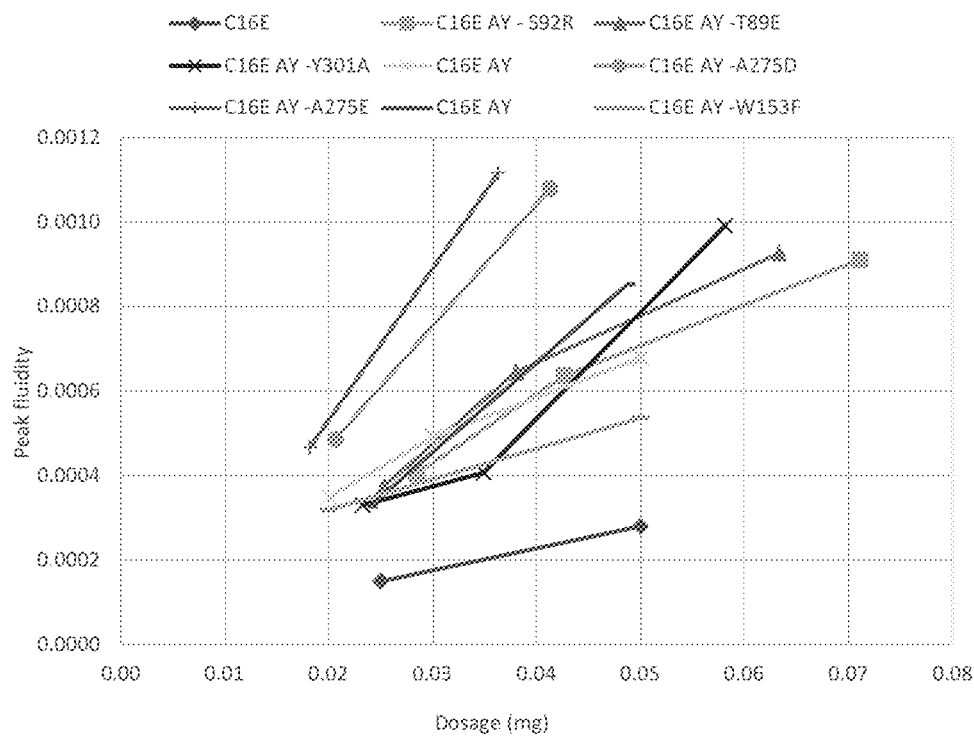
FIG. 3 is a graph showing peak fluidity values per mg enzyme resulting from incubation of the starch substrate with C16E-based α-amylase variants.
Figure 4:
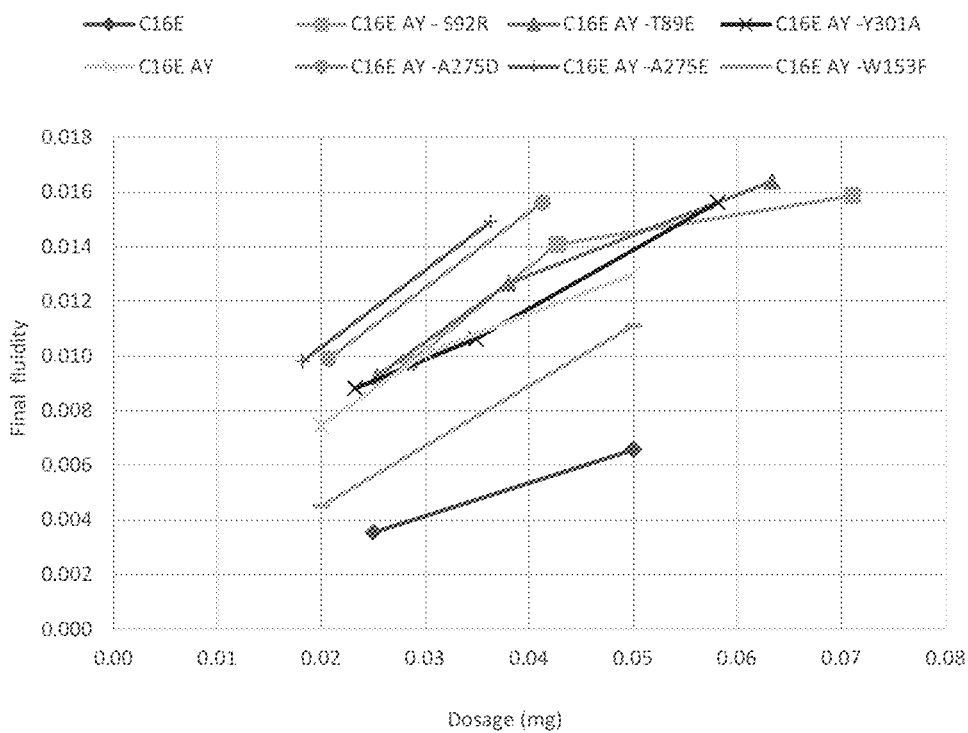
FIG. 4 is a graph showing final fluidity values per mg enzyme resulting from incubation of the starch substrate with C16E-based α-amylase variants.

Peak and final fluidity viscosity was measured as described in Example 1, except that the dosages of enzyme in the assay varied. Peak fluidity values per mg enzyme resulting from incubation of the starch substrate with C16E-based variants C16E are shown in FIG. 3. Final fluidity values are shown in FIG. 4.

Example 5

Additional CspAmy2-v5-Based Variants

The additional CspAmy2-v5-based variants shown in Table 6 were constructed as described in WO 2014/164777. As above, deletions at positions R178 and G179 are indicated by "del (R178, G179)" and amino acid position numbering refers to SEQ ID NO: 1:

TABLE 6

CspAmy2-v5-based variants

| Variant | Mutations |
|---|---|
| CspAmy2-v186 | del (R178, G179) + T38N + N88H + N126Y + T129I + N134M + F153W + L171R + T180D + E187P + I203Y + G476K + G477E |
| CspAmy2-v192 | del (R178, G179) + N126Y + T180D + E187P + I203Y + G476K + G477E |
| CspAmy2-v193 | del (R178, G179) + N126Y + T180D + E187P + I203Y + Y303D + G476K + G477E |
| CspAmy2-v194 | del (R178, G179) + N126Y + F153W + T180D + E187P + I203Y + G476K + G477E |
| CspAmy2-v195 | del (R178, G179) + T38N + N126Y + F153W + T180D + E187P + I203Y + G476K + G477E |
| CspAmy2-v196 | del (R178, G179) + T38N + N126Y + T129I + F153W + T180D + E187P + I203Y + G476K + G477E |

Example 6

Cleaning Performance and Detergent Stability of CspAmy2-v5-Based Variants

The mid- and full-scale cleaning performance of the purified CspAmy2-v5-based variants was analyzed in a microswatch cleaning assay performed as described above, in Example 1. Small-scale and full scale detergent stability was also performed as described above, in Example 1. The results are shown in Tables 7-9:

TABLE 7

Mid-scale cleaning performance of variants CspAmy2-v195 and CspAmy2-v196 compared to commercial benchmarks

| ppm amy-lase | Optical reflectance | | | |
|---|---|---|---|---|
|  | CspAmy2-v195 | CspAmy2-v196 | PREFERENZ™ S 100 | STAINZYME® |
| 0 | 0.172 | 0.172 | 0.172 | 0.172 |
| 0.02 | 0.343 | 0.284 | 0.251 | 0.199 |

TABLE 7-continued

Mid-scale cleaning performance of variants CspAmy2-v195 and CspAmy2-v196 compared to commercial benchmarks

| ppm amylase | Optical reflectance | | | |
|---|---|---|---|---|
| | CspAmy2-v195 | CspAmy2-v196 | PREFERENZ ™ S 100 | STAINZYME ® |
| 0.05 | 0.418 | 0.352 | 0.324 | 0.216 |
| 0.1 | 0.481 | 0.446 | 0.383 | 0.279 |
| 0.3 | 0.562 | 0.540 | 0.515 | 0.338 |
| 0.5 | 0.556 | 0.533 | 0.535 | 0.433 |

TABLE 8

Full-scale cleaning performance of CspAmy2-v5-based variants compared to commercial benchmarks

| Amylase/Variant | Stain | |
|---|---|---|
| | EMPA-161 starch | CFT C-S-28 rice starch |
| nil amylase | 0.045 | 0.329 |
| CspAmy2-v186 | 0.185 | 0.394 |
| CspAmy2-v192 | 0.078 | 0.363 |
| CspAmy2-v193 | 0.150 | 0.366 |
| CspAmy2-v194 | 0.120 | 0.358 |
| CspAmy2-v195 | 0.265 | 0.409 |
| CspAmy2-v196 | 0.270 | 0.409 |
| STAINZYME ® | 0.127 | 0.353 |

TABLE 9

Detergent stability of CspAmy2-v5-based variants compared to commercial benchmarks

| Amylase/Variant | Days under assay conditions | |
|---|---|---|
| | Day 7 | Day 27 |
| CspAmy2-v5 | 49% | 9% |
| CspAmy2-v195 | 78% | 41% |
| CspAmy2-v196 | 84% | 50% |
| STAINZYME ® | 32% | 26% |
| PREFERENZ ™ S 100 | 2% | not measured |

Variants v195 and v196 show improved cleaning performance over benchmarks including STAINZYME® and PREFERENZ™ S 100 at mid- and full-scale on a variety of soils (data for three soils are presented here). The same two variants, v195 and v196, also show superior stability in accelerated stress tests in liquid detergents, compared to benchmarks including CspAmy2-v5, STAINZYME® and PREFERENZ™ S 100.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A recombinant variant of a parent α-amylase comprising:
    a mutation at an amino acid residue corresponding to R377; and
    at least one mutation at an amino acid residue, or residues, corresponding to an amino acid residue selected from the group consisting of N126, F153, T180, E187, and I203;
    wherein the variant α-amylase or the parent α-amylase has at least 95%, amino acid sequence identity relative to SEQ ID NO: 1, which is used for numbering; and
    wherein the variant has increased low pH stability and/or starch liquefaction activity, compared to the parent α-amylase or a reference α-amylase differing from the variant α-amylase only by the absence of the mutations.

2. The variant α-amylase of claim 1, comprising the mutation R377Y; and at least one mutation at an amino acid residue, or residues, corresponding to an amino acid residue selected from the group consisting of N126Y, F153W, T180H, T180D, E187P, and I203Y, using SEQ ID NO: 1 for numbering.

3. The variant α-amylase of claim 1, further comprising a mutation S362A, using SEQ ID NO: 1 for numbering.

4. The variant α-amylase of claim 3, further comprising the mutations N126Y, F153W, T180H, and E187P, using SEQ ID NO: 1 for numbering.

5. The variant α-amylase of claim 1, further comprising a mutation as a position selected from the group consisting of A277, T89, S92 and Y303, using SEQ ID NO: 1 for numbering.

6. The variant α-amylase of claim 1, further comprising a deletion of at least one amino acid residue corresponding to R178, G179, T180, and G181, using SEQ ID NO: 1 for numbering.

7. The variant α-amylase of claim 1, further comprising deletions of amino acid residues corresponding to R178 and G179, or T180 and G181, using SEQ ID NO: 1 for numbering.

8. The variant α-amylase of claim 1, further comprising a mutation at an amino acid residue corresponding to G476, G477, E132, Q167, A277, R458, T459, and/or D460, using SEQ ID NO: 1 for numbering.

9. The variant α-amylase of claim 1, wherein the parental α-amylase is from a Cytophaga species or not from a *Bacillus* species.

10. A method for converting starch to oligosaccharides, comprising contacting starch with effective amount of the variant amylase of claim 1.

11. A composition for liquefying starch comprising the variant amylase of claim 1.

* * * * *

SEQUENCE LISTING

<160> NUMBER OF SEQ ID NOS: 2

<210> SEQ ID NO 1
<211> LENGTH: 485
<212> TYPE: PRT
<213> ORGANISM: Cytophaga sp.

<400> SEQUENCE: 1

```
Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
                20                  25                  30

Ser Ser Val Gly Ile Thr Ala Val Trp Thr Pro Pro Ala Tyr Lys Gly
            35                  40                  45

Thr Ser Gln Ala Asp Val Gly Tyr Gly Pro Tyr Asp Leu Tyr Asp Leu
        50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
                100                 105                 110

Glu Asn Val Thr Ala Val Glu Val Asn Pro Ser Asn Arg Asn Gln Glu
            115                 120                 125

Thr Ser Gly Glu Tyr Asn Ile Gln Ala Trp Thr Gly Phe Asn Phe Pro
        130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
```

```
                    165                 170                 175
Phe Arg Gly Thr Gly Lys Ala Trp Asp Trp Glu Val Ser Ser Glu Asn
                180                 185                 190

Gly Asn Tyr Asp Tyr Leu Met Tyr Ala Asp Ile Asp Tyr Asp His Pro
            195                 200                 205

Asp Val Val Asn Glu Met Lys Lys Trp Gly Val Trp Tyr Ala Asn Glu
        210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
                485

<210> SEQ ID NO 2
<211> LENGTH: 483
<212> TYPE: PRT
<213> ORGANISM: Artificial sequence
<220> FEATURE:
<223> OTHER INFORMATION: Derived from Cytophaga sp.

<400> SEQUENCE: 2

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
```

```
                35                  40                  45
Thr Ser Gln Ala Asp Val Gly Tyr Gly Pro Tyr Asp Leu Tyr Asp Leu
 50                  55                  60
Gly Glu Phe Asn Gln Lys Gly Thr Val Arg Thr Lys Tyr Gly Thr Lys
 65                  70                  75                  80
Gly Glu Leu Lys Ser Ala Val Asn Thr Leu His Ser Asn Gly Ile Gln
                 85                  90                  95
Val Tyr Gly Asp Val Val Met Asn His Lys Ala Gly Ala Asp Tyr Thr
                100                 105                 110
Glu Asn Val Thr Ala Val Glu Val Asn Pro Ser Asn Arg Asn Gln Glu
                115                 120                 125
Thr Ser Gly Glu Tyr Asn Ile Gln Ala Trp Thr Gly Phe Asn Phe Pro
130                 135                 140
Gly Arg Gly Thr Thr Tyr Ser Asn Phe Lys Trp Gln Trp Phe His Phe
145                 150                 155                 160
Asp Gly Thr Asp Trp Asp Gln Ser Arg Ser Leu Ser Arg Ile Phe Lys
                165                 170                 175
Phe Thr Gly Lys Ala Trp Asp Trp Glu Val Ser Ser Glu Asn Gly Asn
                180                 185                 190
Tyr Asp Tyr Leu Met Tyr Ala Asp Ile Asp Tyr Asp His Pro Asp Val
                195                 200                 205
Val Asn Glu Met Lys Lys Trp Gly Val Trp Tyr Ala Asn Glu Val Gly
210                 215                 220
Leu Asp Gly Tyr Arg Leu Asp Ala Val Lys His Ile Lys Phe Ser Phe
225                 230                 235                 240
Leu Lys Asp Trp Val Asp Asn Ala Arg Ala Ala Thr Gly Lys Glu Met
                245                 250                 255
Phe Thr Val Gly Glu Tyr Trp Gln Asn Asp Leu Gly Ala Leu Asn Asn
                260                 265                 270
Tyr Leu Ala Lys Val Asn Tyr Asn Gln Ser Leu Phe Asp Ala Pro Leu
                275                 280                 285
His Tyr Asn Phe Tyr Ala Ala Ser Thr Gly Gly Tyr Tyr Asp Met
                290                 295                 300
Arg Asn Ile Leu Asn Asn Thr Leu Val Ala Ser Asn Pro Thr Lys Ala
305                 310                 315                 320
Val Thr Leu Val Glu Asn His Asp Thr Gln Pro Gly Gln Ser Leu Glu
                325                 330                 335
Ser Thr Val Gln Pro Trp Phe Lys Pro Leu Ala Tyr Ala Phe Ile Leu
                340                 345                 350
Thr Arg Ser Gly Gly Tyr Pro Ser Val Phe Tyr Gly Asp Met Tyr Gly
                355                 360                 365
Thr Lys Gly Thr Thr Thr Arg Glu Ile Pro Ala Leu Lys Ser Lys Ile
                370                 375                 380
Glu Pro Leu Leu Lys Ala Arg Lys Asp Tyr Ala Tyr Gly Thr Gln Arg
385                 390                 395                 400
Asp Tyr Ile Asp Asn Pro Asp Val Ile Gly Trp Thr Arg Glu Gly Asp
                405                 410                 415
Ser Thr Lys Ala Lys Ser Gly Leu Ala Thr Val Ile Thr Asp Gly Pro
                420                 425                 430
Gly Gly Ser Lys Arg Met Tyr Val Gly Thr Ser Asn Ala Gly Glu Ile
                435                 440                 445
Trp Tyr Asp Leu Thr Gly Asn Arg Thr Asp Lys Ile Thr Ile Gly Ser
                450                 455                 460
```

```
Asp Gly Tyr Ala Thr Phe Pro Val Asn Gly Gly Ser Val Ser Val Trp
465                 470                475                480
Val Gln Gln
```